(12) United States Patent
Khalak et al.

(10) Patent No.: US 12,176,106 B1
(45) Date of Patent: *Dec. 24, 2024

(54) LEARNING EXPERT SYSTEM

(71) Applicant: CollectiveHealth, Inc., San Francisco, CA (US)

(72) Inventors: Asif Khalak, Belmont, CA (US); Dara Strauss-Albee, San Francisco, CA (US); Sergio Martinez-Ortuno, Oakland, CA (US)

(73) Assignee: CollectiveHealth, Inc., San Mateo, CA (US)

( * ) Notice: Subject to any disclaimer, the term of this patent is extended or adjusted under 35 U.S.C. 154(b) by 1029 days.

This patent is subject to a terminal disclaimer.

(21) Appl. No.: 17/079,894

(22) Filed: Oct. 26, 2020

Related U.S. Application Data

(63) Continuation of application No. 15/613,005, filed on Jun. 2, 2017, now Pat. No. 10,818,395.

(51) Int. Cl.
| | |
|---|---|
| *G16H 50/20* | (2018.01) |
| *G06N 5/025* | (2023.01) |
| *G06N 5/04* | (2023.01) |
| *G06N 20/00* | (2019.01) |
| *G06Q 40/08* | (2012.01) |

(52) U.S. Cl.
CPC ............. *G16H 50/20* (2018.01); *G06N 5/025* (2013.01); *G06N 5/04* (2013.01); *G06N 20/00* (2019.01); *G06Q 40/08* (2013.01)

(58) Field of Classification Search
CPC .......... G16H 50/20; G06N 5/025; G06N 5/04; G06N 20/00; G06Q 40/08
See application file for complete search history.

(56) References Cited

U.S. PATENT DOCUMENTS

| | | | |
|---|---|---|---|
| 10,192,260 B2* | 1/2019 | Tholl | G06Q 40/08 |
| 10,818,395 B1* | 10/2020 | Khalak | G16H 10/60 |
| 2003/0177139 A1 | 9/2003 | Cameron et al. | |
| 2006/0155725 A1 | 7/2006 | Foster et al. | |
| 2007/0162295 A1* | 7/2007 | Akhtar | G16H 20/40 |
| | | | 705/2 |
| 2010/0082367 A1 | 4/2010 | Hains et al. | |
| 2014/0149130 A1* | 5/2014 | Getchius | G16H 50/20 |
| | | | 705/2 |

(Continued)

FOREIGN PATENT DOCUMENTS

CN 102577533 B 5/2015

OTHER PUBLICATIONS

Non Final Office Action dated Mar. 9, 2020 for U.S. Appl. No. 15/613,005 "Learning Expert System" Khalak, 17 pages.

*Primary Examiner* — James T Tsai
(74) *Attorney, Agent, or Firm* — Lee & Hayes, P.C.

(57) ABSTRACT

In an example, a server associated with a healthcare management service provider can receive first instructions defining rule(s) associated attribute(s) of a claim and/or a target member of a healthcare management service provider. The server can receive second instructions defining a schema for translating the rule(s) into logical expression(s). Using the rule(s) and/or the logical expression(s), a first data entry can be identified. A second data entry can be identified using a model. The server can generate an output identifying the first data entry and the second data entry and can perform an operation based at least in part on the output.

20 Claims, 8 Drawing Sheets

(56) References Cited

U.S. PATENT DOCUMENTS

2015/0278469 A1* 10/2015 Kahlon .................. G16H 50/70
705/3
2015/0332002 A1* 11/2015 Zielinski ................ G06Q 40/08
705/2

* cited by examiner

LEARNING EXPERT SYSTEM

PRIORITY

This Application is a continuation of, and claims priority to, pending U.S. patent application Ser. No. 15/613,005, filed on Jun. 2, 2017, entitled "LEARNING EXPERT SYSTEM", now U.S. Pat. No. 10,818,395, which issued on Oct. 27, 2020, which is fully incorporated by reference herein.

BACKGROUND

Previous expert systems leveraged a plurality of logical rules to evaluate situations. These expert systems were useful in the medical domain, but the complexity associated with such expert systems defeated their usefulness. For instance, previous expert systems had limitations with respect to enabling an expert (i.e., a person who has significant knowledge and/or skill in a particular area) to translate his or her expertise into logical rules for use in the expert system. That is, previous expert systems have shortcomings with respect to enabling an expert to translate his or her knowledge about a particular topic into logical rules for processing data. Furthermore, in previous expert systems, as additional logical rules were added to an expert system that already included a multitude of logical rules, it became difficult to edit and/or update the logical rules. Additionally, as the number of logical rules added to previous expert systems increased, run-time complexity increased, resulting in slow response times for such expert systems.

Advances in expert systems introduced truth maintenance systems, which changed the format of how expert knowledge was input into an expert system. Truth maintenance systems can output inconsistent results and can be difficult to implement. Other advances, such as the incorporation of decision trees and/or learning systems, into expert systems have been helpful in overcoming shortcomings of previous expert systems. However, additional shortcomings remain with respect to easily incorporating expert knowledge into expert systems and efficiently executing the expert systems.

More recently, expert systems have been designed for specific use-cases and perspectives. Generally, such expert systems require artificial intelligence experts. Additionally and/or alternatively, use of such expert systems requires extensive training. Often, such expert systems that have been designed for specific use-cases and perspectives reside in different, inconsistent formats. That is, such expert systems are not usable across multiple, different applications.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
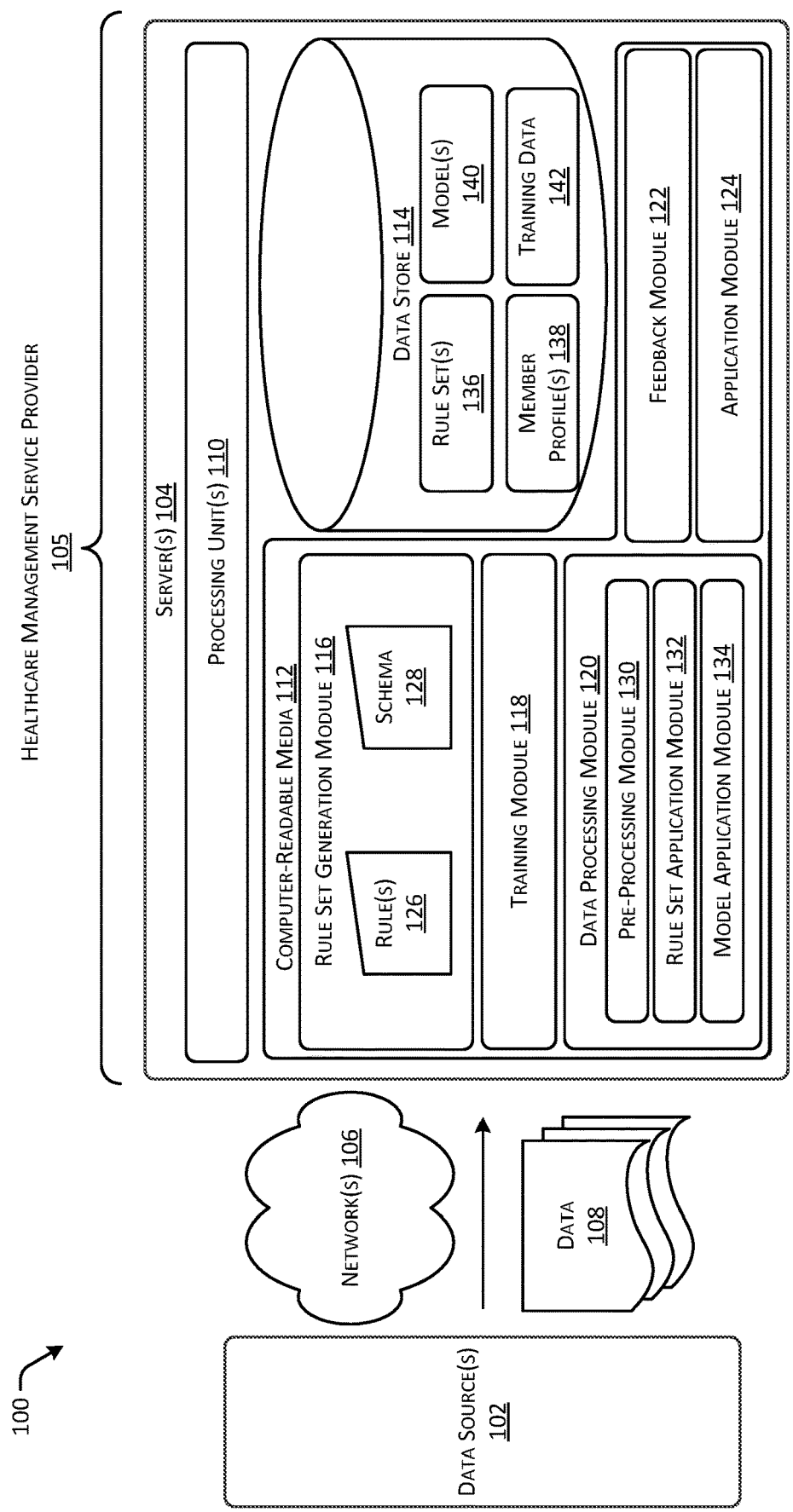
FIG. 1 illustrates an environment for identifying data based on a predefined set of rules that have been translated into logical expression(s) using a predefined schema.

As discussed above, existing expert systems suffer from various shortcomings. For instance, existing expert systems have limitations with respect to enabling an expert (i.e., a person who has significant knowledge and/or skill in a particular area) to translate his or her expertise into logical rules for use in the expert system. Furthermore, to the extent that existing expert systems have been designed for specific use-cases and perspectives, such expert systems reside in different, inconsistent formats. Additionally, expert systems are not easily usable by non-experts (i.e., a person who lacks significant knowledge and/or skill in a particular area) and/or individuals with little or no engineering and/or software background. That is, existing expert systems are not usable across multiple, different applications and/or are not user-friendly for certain users. Additionally, existing expert systems can suffer from slow response time due to the complexity of such expert systems. That is, as the number of logical rules increase in expert systems, run-time complexity increases, and such increases may result in slow response times during execution of such expert systems.

Techniques described herein include systems, methods, and apparatuses that enable users with varying levels of expertise in a particular area and/or varying levels of engineering and/or software knowledge to parse information in a data rich environment. That is, techniques described herein are directed to making expert systems more accessible for users with different types and/or levels of expertise. In some examples, this increased accessibility can be achieved by use of a graphical user interface (GUI) to enable non-experts to input a set of rules, as described below. Furthermore, techniques described herein are directed to making expert systems adaptable so that such expert systems can be used for processing data in various healthcare applications. In some examples, this adaptability can be achieved by enabling programmers to provide instructions that are applicable across multiple applications. Moreover, as described below, techniques described herein enable various computational efficiencies for expert systems. In some examples, such efficiencies can be achieved by leveraging the GUI described above to reduce communication between devices operated by engineers, operations workers, and domain experts and streamline the data analysis process. Additional details associated with the aforementioned benefits are provided below.

Techniques described herein are directed to identifying data in a dataset based on a predefined set of rules that have been translated into logical expressions using a predefined schema. The set of rules can include one or more rules that are used to filter a dataset to identify data that is of a particular interest to an expert-type user. Techniques described herein are directed to a graphical user interface (GUI) that enables an expert-type user to input the set of rules. That is, the set of rules can be user-editable by, for example, expert-type users. For the purpose of this discussion, an expert-type user is a user interested in identifying a particular subset of data in a data rich environment. In some examples, an expert-type user can be an expert. That is, an expert-type user can have significant knowledge and/or skill in a particular area. For instance, as non-limiting examples, an expert-type user in the healthcare industry can include a doctor, a surgeon, a specialist, etc. An expert-type user in the insurance industry can include, but is not limited to, a claims adjudicator, a claims adjuster, or a plan developer. In other examples, an expert-type user may not have significant knowledge and/or skill in a particular area but can generally be interested in identifying a particular subset of data in a data rich environment. Such an expert-type user can include, but is not limited to, a researcher, a scholar, etc.

A schema can be used to translate the set of rules into logical expression(s), which can be used to filter the dataset to identify data that satisfies the set of rules. The schema can be used to translate the set of rules into computer-executable logical expression(s). In at least one example, a schema can be provided by a power user. For the purpose of this discussion, a power user can use advanced features of computing hardware, operating systems, programs, websites, etc. that are not used by average computer users or, in some examples, expert-type users. In at least one example, a power user can have knowledge to make broad and general use of computer programs but may not be a programmer.

Techniques described herein are directed to accessing data in a data set and applying logical expression(s) to the dataset to generate a rules-based output. That is, a schema can be used to translate a set of rules into logical expression(s), which are applied to data in a data set to generate a rules-based output. At substantially the same time as the logical expression(s) are being used to generate the rules-based output, techniques described herein can additionally apply a model, which can be trained via a machine learning mechanism, to the dataset. The model can output a prediction identifying data that is of particular interest to the expert-type user (i.e., the model-based output). The rules-based output and the model-based output can be aggregated to form an aggregated output. The aggregated output may be utilized to present relevant information, depending on a particular healthcare application to which the aggregated output pertains.

As a non-limiting example, an expert-type user can be a claims processor with extensive knowledge on insurance claims. In the example, the expert-type user can be interested in identifying insurance claims associated with patients between the ages of 15 and 60, in a particular geographical area, for a treatment of a particular condition. For instance, such insurance claims can be indicative of a health event. Techniques described herein enable the claims processor (who may or may not have any engineering and/or software expertise) interact with the GUI to input a set of rules. That is, the claims processor can interact with the GUI to indicate that he or she is interested in identifying insurance claims associated with patients between the ages of 15 and 60, in the particular geographical area, for the treatment of a particular condition. When the rules are input, the schema can be used to convert the rules into logical expressions.

Techniques described herein can apply logical expressions derived from the set of rules to identify insurance claims that are associated with patients between the ages of 15 and 60, in the particular geographical area, for the treatment of the particular condition. That is, the rules-based output can identify one or more insurance claims associated with patients between the ages of 15 and 60, in the particular geographical area, for the treatment of the particular condition. A model can be used substantially simultaneously to process the same set of insurance claims to predict one or more insurance claims that are associated with the health event. The rules-based output and the model-based output can be aggregated into a list of insurance claims that are indicative of the health event. The claims processor can then use the aggregated output for various purposes and/or applications, as described herein. That is, techniques described herein enable the claims processor to interact (e.g., search, manipulate, etc.) with data that would be too difficult and/or impossible (e.g., due to volume or complexity) without the techniques described herein.

As described above, techniques described herein may be applicable across multiple applications. In at least one example, techniques described herein may be applicable across various healthcare applications. For instance, techniques described herein can be used for healthcare program navigation and management. In at least one example, a healthcare management service provider can leverage the techniques described herein to identify individuals who may benefit from a particular service offered by the healthcare management service provider. For the purpose of this discussion, such individuals may be referred to as target members. In some examples, the individuals can be members of the healthcare management service provider. That is, the individuals have an account through which the individuals can access services offered by the healthcare management service provider. In additional and/or alternative examples, the individuals can be potential members. That is, the individuals may not have an account through which the individuals can access services offered by the healthcare management service provider, but can benefit from a particular service offered by the healthcare management service provider.

In an example where techniques described above are utilized for identifying individuals that can benefit from services of the healthcare management service provider, the set of rules can identify attributes of a particular profile. For instance, the particular profile can correspond to a profile of one or more individuals (i.e., target members) that would benefit from particular program(s) and/or resource(s) offered by the healthcare management service provider. The dataset can correspond to individual data associated with claims associated with individuals, healthcare program authorizations associated with individuals, healthcare program utilization by individuals, engagement of individuals, preferences of individuals, medical data associated with individuals, etc. In some examples, the dataset can include data associated with members (e.g., member data) and/or data associated with potential members (e.g., potential member data). Techniques described herein can apply the dataset to logical expression(s) representative of the set of rules and can generate a rules-based output. The rules-based output can identify one or more individuals having the particular profile. As described above, the dataset can be applied to a model, which can be trained using a machine learning mechanism, to generate a model-based output at a substantially same time as the rules-based output is generated. The model-based output can identify one or more individuals that are likely to have the particular profile. Based on the rules-based output and the model-based output, techniques described herein can leverage various tools to connect identified individuals to particular program(s) and facilitate relevant engagement so that the identified individuals are able to take advantage of services that are available via the healthcare management service provider.

For instance, in at least one example, techniques described herein enable a healthcare management service provider to send and/or provide various communications to individuals identified via the rules-based output and/or the model-based output. For instance, the healthcare management service provider can send emails, text messages, and/or push notifications to individuals identified via the rules-based output and/or the model-based output, send messages to individuals identified via the rules-based output and/or the model-based output via a website portal and/or an application, call individuals identified via the rules-based output and/or the model-based output, etc. In at least one example, one or more target members can be associated with a same health characteristic (e.g., diagnosis, disease, condition, etc.) and the healthcare management service provider can send communications to the target members offering a service to guide the individuals through programs for addressing the health characteristic. Additionally and/or alternatively, techniques described herein enable a healthcare management service provider to recommend product partners, unknown (to the individual(s)) healthcare program benefits, healthcare program design incentives, etc. to individuals identified via the rules-based output and/or the model-based output. Moreover, techniques described herein can enable a healthcare management service provider to determine and recommend healthcare program changes to an employer and/or employers associated with individuals identified via the rules-based output and/or the model-based output.

In some examples, an employer can leverage techniques described herein to provide healthcare benefits to their employees. For instance, in such examples, an employer can collaborate with the healthcare management service provider so that the healthcare management service provider identifies employees of the employer that would benefit from particular healthcare programs (e.g., offered by the employer and/or the healthcare management service provider). In such examples, the healthcare management service provider can provide resource(s) to the employers to facilitate the particular healthcare programs for the identified employees. The healthcare management service provider can interact with the employers in a same and/or similar manner as described above with respect to individual individuals.

Additionally and/or alternatively, techniques described herein can be used for fraud detection. For instance, in at least one example, techniques described herein can be used to identify fraudulent claims. A claim can identify an individual who received a service, the service provided, a service provider that provided the service, a date associated with the service, a time associated with the service, a location associated with the service, a cost associated with the service, a code associated with the service, etc. In at least one example, the set of rules can identify attributes of a fraudulent claim. Techniques described herein can access a dataset associated with a plurality of claims, apply the dataset to logical expression(s) representative of the set of rules, and generate a rules-based output. The rules-based output can correspond to one or more claims that are identified as being fraudulent. As described above, a model-based output can identify one or more claims that are likely to be fraudulent. Based on the rules-based output and the model-based output, techniques described herein can identify fraudulent claims.

Moreover, techniques described herein can be used for analyzing claims data. For instance, techniques described herein can be utilized for claim mapping, validation, and/or routing. In at least one example, the set of rules can identify attributes of a classification of a claim. Techniques described herein can access a dataset associated with a plurality of claims, apply the dataset to logical expression(s) representative of the set of rules, and generate a rules-based output. The rules-based output can identify one or more claims that are associated with the classification. As described above, a model-based output can identify one or more claims that are likely to be associated with the classification. Based on the rules-based output and the model-based output, techniques described herein can classify claims, map claims to particular classifications, validate previous classifications of claims, etc. In at least one example, claim classification may be useful for grouping claims by events and/or episodes. In an additional and/or alternative example, claim classification can be useful for initiating an adjudication process to adjudicate claims based on respective classifications. That is, in at least one example, techniques described herein can be useful for value-based care applications.

Additionally and/or alternatively, techniques described herein can be used for auditing purposes. For instance, techniques described herein can be utilized for verifying and auditing healthcare data sources and/or healthcare reporting data. Furthermore, techniques described herein can be used as an aspect of a document search system. For instance, the techniques described herein can be useful for determining a document key associated with a particular data item. Based on the document key, additional information can be retrieved via a search. For instance, based at least in part on classifying a support ticket (e.g., a request for support) with a particular class, additional information for responding to such a support ticket can be accessed via a search using the particular class. Or, based at least in part on classifying a benefit with a particular benefit class, additional information for describing the benefit can be accessed via a search using the particular benefit class.

As described above, techniques described herein are applicable across various healthcare applications. In some examples, data relevant to different healthcare applications can be processed in different sessions and/or at different levels of the system described herein. In addition to being applicable across various healthcare applications, techniques described herein provide improvements to existing expert systems described above. For instance, techniques described herein enable individuals having little to no engineering and/or software background to parse information in a data rich environment by leveraging a graphical user interface (GUI) to input a set of rules that are associated with a particular healthcare application of interest. That is, techniques described herein enable such individuals to manipulate rules and filters without having any prior knowledge of the source code. Furthermore, techniques described herein liberate individuals from having to write formal logical expressions by utilizing a schema that understands common-sense language that such individuals use to input the set of rules and translates the common-sense language to logical expression(s) which can be used to process dataset(s). Additionally, techniques described herein enable such individuals to easily modify and/or update the set of rules. Moreover, techniques described herein eliminate, or reduce, the reliance on programmers to serve as intermediaries between individuals interested in extracting data from datasets and the datasets that the individuals are interested in evaluating. That is, techniques described herein enable expert-type users to easily and efficiently translate their expertise into logical rules for use in processing data.

Furthermore, techniques described herein are directed to a GUI that is used for inputting a set of rules, as described above. By using a GUI that feeds a schematic approach to analyzing data, techniques described herein reduce the risk of misconfiguration and data manipulation and enhance security. For instance, an expert-type user's query (i.e., request to identify data of interest to the expert-type user) is separated from the dataset that the schema parses and such separation helps protect the integrity of the data in the dataset so that other users can run their own queries without concerns that the dataset has been affected by prior uses of the techniques described herein. Such separation also secures private information and reduces security risks. Moreover, the GUI described herein reduces the processing time required to process data using the logical expression(s) by reducing communication between devices operated by engineers, operations workers, and domain experts and streamlining the data analysis process. That is, techniques described herein are helpful for streamlining the processes by which rules are input into an expert system and provide computational efficiencies for processing datasets based on such rules. As a result, the techniques described herein improve the performance of computing devices that are processing datasets based on such rules.

In addition to improving the performance of computing devices, the GUI described herein can reduce expert system development time by reducing existing operational inefficiencies caused by communication between engineers, operations workers, and domain experts. That is, as described above, existing expert systems require significant investments by engineers, operations workers, and domain experts to translate queries associated with particular domains into logical expressions. The GUI described herein enables expert-type users, with various engineering and/or software backgrounds, to input rule(s), which can be translated into logical expressions, which are applicable to their particular query. As a result, techniques described herein can provide operational efficiencies in addition to computational efficiencies, as described above.

FIG. 1 illustrates an environment 100 for identifying data based on a predefined set of rules that have been translated into logical expressions using a predefined schema. As illustrated, environment 100 includes data source(s) 102 communicatively coupled to server(s) 104 via network(s) 106.

Data source(s) 102 can include third-party system(s) that provide data 108 to the server(s) 104. Data source(s) 102 can include system(s) associated with healthcare program provider(s), employer(s), and/or member(s). For instance, a data source 102 associated with a healthcare benefit provider can provide data 108 associated with claims, data 108 associated with utilization of particular healthcare programs and/or ancillary products (e.g., goods and/or services) provided by the healthcare benefit provider, data 108 associated with engagement of users of healthcare programs and/or ancillary products (e.g., goods and/or services) provided by the healthcare benefit provider, etc. For the purpose of this discussion, a healthcare program can include one or more policies that govern adjudication and reimbursement of healthcare claims relating to dental services, vision services, pharmacy services, and medical services. In at least one example, a healthcare program can include one or more policies directed to the substantiation of claims related to spending accounts such as, but not limited to, flexible spending accounts, health savings accounts, etc. Additionally and/or alternatively, a data source 102 associated with an employer can provide data 108 associated with healthcare programs offered by the employer for the benefit of its employees, etc. Further, a data source 102 associated with a member can provide data 108 associated with member preferences, member health records, etc.

As described above, environment 100 can be associated with server(s) 104. The server(s) 104 can be associated with a healthcare management service provider 105. The healthcare management service provider 105 can manage various aspects of healthcare on behalf of members that subscribe to the healthcare management service provider 105. For instance, the healthcare management service provider 105 can assist members in navigating healthcare program coverage, healthcare program programs, and/or unique care needs. The healthcare management service provider 105 can assist members with processing claims. Additionally and/or alternatively, the healthcare management service provider 105 can help connect members to healthcare programs that are determined to benefit the members and fuel engagement between the members and their healthcare programs. As described above, additionally and/or alternatively, the healthcare management service provider 105 can interact with employers to manage various aspects of healthcare on behalf of the employers.

Each of the server(s) 104 can be any type of server, such as a network-accessible server. Server(s) 104 can include processor(s) 110, computer-readable media 112, and a data store 114. Processor(s) 110 can represent, for example, a CPU-type processing unit, a GPU-type processing unit, a Field-Programmable Gate Array (FPGA), another class of Digital Signal Processor (DSP), or other hardware logic components that can, in some instances, be driven by a CPU. For example, and without limitation, illustrative types of hardware logic components that can be used include Application-Specific Integrated Circuits (ASICs), Application-Specific Standard Products (ASSPs), System-on-a-Chip Systems (SOCs), Complex Programmable Logic Devices (CPLDs), etc. In at least one example, an accelerator can represent a hybrid device, such as one from XILINX or ALTERA that includes a CPU embedded in an FPGA fabric. In various embodiments, the processor(s) 110 can execute one or more modules and/or processes to cause the server(s) 104 to perform a variety of functionalities, as set forth above and explained in further detail in the following disclosure. Additionally, each of the processor(s) 110 can possess its own local memory, which also can store program modules, program data, and/or one or more operating systems.

Depending on the exact configuration and type of the server(s) 104, the computer-readable media 112 can include computer storage media and/or communication media.

Computer storage media can include volatile memory, nonvolatile memory, and/or other persistent and/or auxiliary computer storage media, removable and non-removable computer storage media implemented in any method or technology for storage of information such as computer readable instructions, data structures, program modules, or other data. Computer memory is an example of computer storage media. Thus, computer storage media includes tangible and/or physical forms of media included in a device and/or hardware component that is part of a device or external to a device, including but not limited to random-access memory (RAM), static random-access memory (SRAM), dynamic random-access memory (DRAM), phase change memory (PRAM), read-only memory (ROM), erasable programmable read-only memory (EPROM), electrically erasable programmable read-only memory (EEPROM), flash memory, compact disc read-only memory (CD-ROM), digital versatile disks (DVDs), optical cards or other optical storage media, miniature hard drives, memory cards, magnetic cassettes, magnetic tape, magnetic disk storage, magnetic cards or other magnetic storage devices or media, solid-state memory devices, storage arrays, network attached storage, storage area networks, hosted computer storage or any other storage memory, storage device, and/or storage medium that can be used to store and maintain information for access by a computing device.

In at least one example, the computer storage media can include non-transitory computer-readable media. Non-transitory computer-readable media can include volatile and nonvolatile, removable and non-removable tangible, physical media implemented in technology for storage of information, such as computer readable instructions, data structures, program modules, or other data. Computer-readable media 112 is an example of non-transitory computer-readable media. Non-transitory computer-readable media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible, physical medium which can be used to store the desired information and which can be accessed by the server(s) 104. Any such non-transitory computer-readable media can be part of the server(s) 104.

In contrast, communication media includes computer readable instructions, data structures, program modules, or other data in a modulated data signal, such as a carrier wave, or other transmission mechanism. As defined herein, computer storage media does not include communication media.

The computer-readable media 112 can include one or more modules and data structures including, for example, a rule set generation module 116, a training module 118, a data processing module 120, a feedback module 122, and an application module 124. The one or more modules and data structures can be in the form of stand-alone applications, productivity applications, an operating system component, or any other application or software module.

The rule set generation module 116 can be configured to generate one or more rule sets. In at least one example, the rule set generation module 116 can receive instructions associated with one or more rules 126. In at least one example, the rule(s) 126 can be articulated by an expert-type user via a GUI, an example of which is shown and described below with reference to FIG. 2. In some examples, multiple expert-type users can input rules via the GUI at substantially the same time via different devices operated by the multiple expert-type users, which may be remotely located. That is, in some examples, the GUI can be collaborative and/or distributed.

In at least one example, the rule(s) 126 can be associated with a particular healthcare application. That is, the rule(s) 126 can be defined by one or more expert-type users so that the data processing module 120 can leverage the rule(s) 126 to filter a dataset and identify data that is relevant to the particular healthcare application. For instance, one or more expert-type users can desire to identify individuals that are associated with a profile. In such an example, the rule(s) 126 can be associated with attribute(s) of the profile. The attribute(s) can include, but are not limited to, claims (i.e., claims associated with previously provided healthcare services), claim authorizations (i.e., authorizations previously provided by a medical professional for a particular healthcare service), healthcare program utilizations (i.e., date stamp, time stamp, count, etc. associated with a particular healthcare service), individual engagements (i.e., communications from individuals), individual preferences, or health records of individuals. In addition to defining the attribute(s), the one or more expert-type users can define parameter(s) for each attribute.

Additionally and/or alternatively, one or more expert-type users can desire to identify fraudulent healthcare benefit claims. In such an example, the rule(s) 126 can be associated with attribute(s) of a fraudulent healthcare benefit claim. The attribute(s) can include, but are not limited to, dates associated with claims, locations associated with services documented in claims, services associated with claims, providers associated with claims, costs associated with services documented in claims, or codes associated with services documented in claims. In addition to defining the attribute(s), the one or more expert-type users can define parameter(s) for each attribute.

Or, one or more expert-type users can be interested in classifying claims. In such an example, the rule(s) can be associated with attribute(s) of a particular classification of a claim. The attribute(s) can include, but are not limited to, dates associated with claims, locations associated with services documented in claims, services associated with claims, providers associated with claims, costs associated with services documented in claims, or codes associated with services documented in claims. In addition to defining the attribute(s), the one or more expert-type users can define parameter(s) for each attribute.

In some examples, the rule set generation module 116 can process the rule(s) 126 using a set of pre-defined criteria to determine the validity of the rule(s) 126. For instance, the rule set generation module 116 can determine that the rule(s) 126 are input in a datatype that can be processed via schema 128 based on the set of pre-defined criteria. Additionally and/or alternatively, the rule generation module 116 can determine that individual rules in the rule(s) 126 are mutually exclusive based on the set of pre-defined criteria. Or, the rule set generation module 116 can determine restriction(s) on certain attribute(s) based on the set of pre-defined criteria.

In addition to receiving the rule(s) 126, the rule set generation module 116 can receive schema 128. In at least one example, the schema 128 can translate the rule(s) 126 into logical expression(s) which can be used by the data processing module 120 to process datasets. That is, the schema 128 can translate the user-editable rule(s) 126 into computer-executable logical expressions. In at least one example, the schema 128 can be provided by a power user, as described above. In some examples, a power user can be the same user as the expert-type user and, in other examples, the power user can be a different user than the expert-type user. In some examples, each user (e.g., the power user, expert-type user, etc.) can have different access-control settings. In at least one example, the schema 128 can be domain specific (i.e., specific to a particular record format, data format, etc.). That is, in such an example, the schema 128 can be utilized to translate different sets of rules and/or different types of data.

A non-limiting example of a schema is provided below in Table 1.

TABLE 1

| Name | Group | GroupType | ElementName | ElementType |
|---|---|---|---|---|
| C1_1 | C1 | key_value_list | one | icd_code |
| C1_2 | C1 | key_value_list | two | icd_code |
| C1_3 | C1 | key_value_list | three | string |
| C2_1 | C2 | key_value_list | one | Age |
| C2_2 | C2 | key_value_list | two | Age |
| C3_1 | C3 | list | one | Int |

In at least one example, a power user can input the schema 128 via a GUI. In some examples, the GUI can include a spreadsheet including a plurality of columns and a plurality of rows. In at least one example, unlike the GUI described above with reference to inputting the rule(s) 126, the GUI for inputting the schema 128 can have a single row per column relationship. In some examples, the GUI for inputting the schema 128 can be collaborative and/or distributed. That is, in some examples, the GUI for inputting the schema 128 can be accessible by remotely located devices operated by different power users at a substantially same time.

The rule set generation module 116 can apply the schema 128 to the rule(s) 126. That is, the rule set generation module 116 can translate each rule 126 into a logical expression based on definitions that exist in the schema 128. For instance, if an expert-type user defines a rule to include a date range for a certain medical procedure, the schema 128 can indicate that values that were entered are dates so that the data processing module 120 can process the values as such. Based at least in part on applying the schema 128 to the rule(s) 126, the rule set generation module 116 can store a resulting rule set in a machine-readable format in the data store 114.

In at least one example, the rule set generation module 116 can bind a function to each rule of a rule set. The data processing module 120 can call the function to run the corresponding rule against a dataset. In some examples, prior to binding the function to each rule of the rule set, the rule set generation module 116 can perform a rule validation check so that each rule is in an expected format such that the data processing module 120 can call the proper function for applying a rule to a dataset. A function that is bound to a rule can be stored with the corresponding rule in the data store 114. The resulting rule set (i.e., rules bound with functions) can be stored in a machine-readable format in the data store 114. For the purpose of this discussion, a resulting rule set (i.e., rules bound with functions) can be called a processed rule set.

The training module 118 can be configured to train a model via a machine learning mechanism. A machine learning mechanism can build, modify, or otherwise utilize a model that is created from example inputs and/or associated outputs, and makes predictions or decisions using the model. In at least one example, a model can be used to predict data items of a dataset that are likely to satisfy an outcome associated with a particular healthcare application. In such an example, the model can be trained using supervised learning algorithms (e.g., artificial neural networks, Bayesian statistics, hidden Markov models, Kalman filters, regression, support vector machines, decision trees, classifiers, k-nearest neighbor, etc.), unsupervised learning algorithms (e.g., association rule learning, hierarchical clustering, cluster analysis, etc.), semi-supervised learning algorithms, deep learning algorithms, etc. Additional details associated with training such a machine learning mechanism are described below with reference to FIG. 3.

In at least one example, the training module 118 can access a dataset wherein individual data items in the dataset are labeled with a label that corresponds to an outcome associated with a particular healthcare application. For instance, a particular claim that is fraudulent is labeled as being fraudulent. Or, a particular claim that is associated with a mental health classification is labeled as such. In some examples, the training module 118 can access a dataset and can apply a set of rules for labeling individual data items in the dataset. In other examples, the training module 118 can access a dataset that includes previously labeled data items (e.g., manually labeled). In some examples, the training module 118 can access the dataset from the data store 114.

The training module 118 can leverage the machine learning mechanism to train a model that identifies particular data items in a dataset. For instance, in at least one example, the training module 118 can leverage the machine learning mechanism to train a model that identifies individuals that are associated with a particular profile. That is, in such an example, the particular profile can correspond to an outcome that is relevant to a healthcare application associated with healthcare program navigation and/or management. In such an example, the training module 118 can leverage one or more attributes associated with data of individuals and can apply weight(s) to the one or more attributes to determine which attribute(s) of the one or more attributes and/or which weight(s) predict individuals that are associated with the particular profile with a level of accuracy above a predetermined threshold. The one or more attributes can be associated with claims, claim authorizations, healthcare program utilizations, engagements, preferences, health records, etc.

Alternatively, in at least one example, the training module 118 can leverage the machine learning mechanism to train a model that identifies individual claims that are likely to be fraudulent. That is, in such an example, the fraudulent claim can correspond to an outcome that is relevant to a healthcare application associated with fraud detection. In such an example, the training module 118 can leverage one or more attributes associated with claims and can apply weight(s) to the one or more attributes to determine which attribute(s) of the one or more attributes and/or which weight(s) predict individual claims that are fraudulent at a level of accuracy above a predetermined threshold. The one or more attributes can be associated with dates associated with claims, locations associated with services documented in claims, services associated with claims, providers associated with claims, costs associated with services documented in claims, codes associated with services documented in claims, etc.

Or, in at least one example, the training module 118 can leverage the machine learning mechanism to train a model that predicts classifications associated with individual claims. That is, in such an example, a classification of a claim can correspond to an outcome that is relevant to a healthcare application associated with healthcare benefit claim mapping, validation, and/or routing. In such an example, the training module 118 can leverage one or more attributes associated with classifications of claims and can apply weight(s) to the one or more attributes to determine which attribute(s) of the one or more attributes and/or which weight(s) are used to predict respective classifications of individual claims at a level of accuracy above a predetermined threshold. The one or more attributes can be associated with dates associated with claims, locations associated with services documented in claims, services associated with claims, providers associated with claims, costs associated with services documented in claims, codes associated with services documented in claims, etc.

Resulting model(s) can be stored in the data store 114. In at least one example, each model can be mapped to, or otherwise associated with, a particular healthcare application. Accordingly, when the particular healthcare application is being utilized to identify data in a dataset, the corresponding model can be accessed by the data processing module 120, as described below.

The data processing module 120 can access a dataset and can process the dataset to identify data that is of interest for a particular healthcare application. That is, an expert-type user can input rule(s) 126, which the data processing module 120 can leverage to conduct a search over a dataset to identify data that satisfies such rule(s) 126. The data processing module 120 can include a pre-processing module 130, a rule set application module 132, and a model application module 134. In at least one example, instructions associated with the data processing module 120 can be provided by a programmer. That is, in such an example, a programmer can provide instructions for processing datasets via the rule set application module 132 and the model application module 134. Such instructions can be applicable to more than one set of rules and/or more than one schema. In at least one example, programmers can have different access-control settings than expert-type users and/or power users.

In at least one example, the pre-processing module 130 can receive data 108 from one or more data sources 102. The data 108 from the one or more data sources 102 can be compiled into a dataset for processing. In at least one example, the pre-processing module 130 can access data from the data store 114 and can aggregate data from the data store 114 with data 108 received from the one or more data sources 102. The dataset, as described above, can include data relevant to a particular healthcare application. For instance, a dataset can include member data, potential member data, claims data, data associated with healthcare programs, data associated with service(s) offered by the healthcare management service provider, etc.

In at least one example, the pre-processing module 130 can convert data items in the dataset into digestible data using a predefined programming language (e.g., python, R, C, C++, Java, SparkQL, etc.). For instance, in some examples, the pre-processing module 130 can arrange data 108 from the data source(s) 102 and/or data from the data store 114 in a tabular format. In such examples, individual rows of a table can represent individual data entries. Depending on the particular healthcare application, a data entry can correspond to a data item associated with an individual (e.g., a member, a potential member, etc.), a claim, etc. That is, the pre-processing module 130 can arrange data 108 from the data source(s) 102 and/or data from the data store 114 in a tabular format such that a plurality of data items associated with individuals, a plurality of claims, etc. can be processed via the processes described below. Additionally and/or alternatively, the pre-processing module 130 can arrange data 108 from the data source(s) 102 into a non-tabular format, such as a serialized object format in various markup languages (e.g., JSON, yaml, etc.). In some examples, the pre-processing module 130 can apply filters to a dataset to eliminate portions (e.g., column(s), row(s), etc.) that are not relevant to a particular search.

In at least one example, the pre-processing module 130 can generate feature(s) that can be derived from data 108 received from the data source(s) 102. For instance, the pre-processing module 130 can generate an age feature based on a date of birth extracted from data 108 received from the data source(s) 102. Or, in another example, the pre-processing module 130 can aggregate individual data 108 received from the data source(s) 102 (e.g., combine multiple data codes and identify a most severe code corresponding to a serious medical condition as a representative code, aggregate transactions over a predetermined period of time, etc.). In some examples, the pre-processing module 130 can map, or otherwise associate, one or more features to the data items in the dataset.

The rule set application module 132 can apply the rule(s) 126 to the dataset by applying a corresponding processed rule set to the dataset. In at least one example, the rule set application module 132 applies each rule of the processed rule set to individual data entries in the dataset to determine whether each data entry satisfies the rule. That is, in at least one example, the rule set application module 132 calls a function corresponding to a particular rule and, responsive to making the call for the function, evaluates a data entry using the particular rule. As an example, the rule set application module 132 can call a function associated with a particular rule and can apply the particular rule to a claim to determine whether the claim satisfies the particular rule. Or, the rule set application module 132 can call a function associated with a particular rule and apply the particular rule to a data entry associated with an individual (e.g., a member, a potential member, etc.) to determine whether the member data satisfies the particular rule.

The rule set application module 132 can repeat the aforementioned process for each rule in the rule(s) 126. That is, the rule set application module 132 can apply each rule in the rule(s) 126 to a data entry to determine whether the data entry satisfies all of the rule(s) 126. Based at least in part on determining that a data entry of the dataset satisfies the rule(s) 126, the rule set application module 132 can flag the data entry. The rule set application module 132 can repeat the aforementioned process for each data entry in a dataset. Flagged data entries can be identified in an output of the rule set application module 132. That is, a rules-based output can identify one or more flagged data items. Additional details associated with applying the rule(s) 126 to the dataset are described below with reference to FIG. 4.

The model application module 134 can apply a model to the dataset. In at least one example, the rule set application module 132 and the model application module 134 can process the dataset in parallel (i.e., at substantially the same time). The model application module 134 can identify one or more data entries in the dataset that are likely to be of interest in view of a particular healthcare application. That is, the model application module 134 can predict one or more data entries that are associated with an outcome of a particular healthcare application. In some examples, the model application module 134 can output a confidence score in association with a data entry of the one or more data entries. In at least one example, the model application module 134 can flag the one or more data entries that are determined to likely be of interest in view of the particular healthcare application. In an additional and/or alternative example, the model application module 134 can flag data entry(s) that are associated with confidence values above a threshold value, in a predetermined range of confidence values, etc. The output of the model application module 134 can be a model-based output. That is, the model-based output can include one or more flagged data entries. In some examples, the one or more flagged data entries can be associated with respectively corresponding confidence values.

The data processing module 120 can access the rules-based output and the model-based output and can combine the rules-based output and the model-based output. In some examples, the rules-based output and the model-based output can be associated with the same flagged data entry(s). In other examples, the rules-based output and the model-based output can be associated with one or more different flagged data entry(s). In such examples, the model-based output can supplement the rules-based output. In at least one example, the data processing module 120 can leverage conflict resolution policies to resolve conflicts between the rules-based output and the model-based output. That is, in some examples, the data processing module 120 can leverage one or more conflict resolution policies to prioritize the rules-based output over the model-based output or vice versa. In at least one example, the data processing module 120 can apply probabilistic fusion and/or other conditions, which can be integrated into the conflict resolution policies. Additional details associated with processing a dataset are described below with reference to FIGS. 4 and 5.

The feedback module 122 can access the output of the data processing module 120 (e.g., the rules-based output and/or the model-based output) and can utilize the output to update the model. That is, feedback module 122 can leverage the output of the data processing module 120 to make adjustments to which attribute(s) and/or weight(s) are used for predicting which data is likely to be of interest in view of a particular healthcare application. In some examples, the feedback module 122 can leverage the output of the data processing module 120 to recommend new rules to add to the rule(s) 126.

In at least one example, the feedback module 122 can add data to the model-based output that provides a context associated with the model-based output. In some examples, the context can identify data items in a dataset, benchmark data derived from a dataset associated with a population, etc. In at least one example, the feedback module 122 can aggregate the model-based output and the data added to the model-based output to present information and/or statistics or data derived from the information in a human-understandable format (e.g., tables, charts, graphs, etc.). In some examples, one or more machine learning mechanisms can be utilized to determine how to present the information and/or statistics or data derived from the information in the human-understandable format. Additionally and/or alternatively, the feedback module 122 can leverage the model-based output (with or without the additional data) and a model-regression, model-training, etc. to update the model as described above.

The application module 124 can access the output of the data processing module 120 (e.g., the rules-based output and the model-based output) and can utilize the output for a particular healthcare application. As described above, the output can be used for healthcare applications such as, but not limited to, healthcare program navigation and/or management, fraud detection, claim mapping, validation, and/or routing, auditing, search strategies, etc., as described above.

As described above, in at least one example, the rule(s) 126 and/or model can be associated with a particular healthcare application. That is, if the particular healthcare application is associated with healthcare program navigation and/or management, the rule(s) 126 and/or model can be associated with profile(s) for identifying individuals that can benefit from healthcare program navigation and/or management. In such an example, the application module 124 can utilize the output of the data processing module 120 to target identified individuals for healthcare program navigation and/or management, as described above. Or, if the particular healthcare application is associated with claim fraud detection, the rule(s) 126 and/or model can be associated with attribute(s) of fraudulent claims. In such an example, the application module 124 can utilize the output of the data processing module 120 to identify fraudulent healthcare benefit claims. Additionally and/or alternatively, if the particular healthcare application is associated with claim mapping, validation, and/or routing, the rule(s) 126 and/or model can be associated with attribute(s) of classifications of healthcare benefit claims. In such an example, the application module 124 can utilize the output of the data processing module 120 to classify healthcare benefit claims for mapping, validating, and/or routing healthcare benefit claims.

The server(s) 104 can be associated with a data store 114, as described above. In some examples, the data store 114 can include one or more databases, such as a rule set(s) database 136, a member profile(s) database 138, a model(s) database 140, and a training data database 142. In at least one example, the data store 114 can be integral to the server(s) 104, as shown in FIG. 1. In other examples, the data store 114 can be communicatively coupled to the server(s) 104.

The rule set(s) database 136 can store rule set(s) output by the rule set generation module 116. Each rule set can be associated with a particular healthcare application, as described above. As described above, a rule set can include one or more rules 126 which have been translated into logical expression(s) (i.e., a rule set). Each of the rule(s) can be bound to a function that can be called by the rule set application module 132 for processing datasets. As described above, the resulting rule set (i.e., with bound functions) can be called a processed rule set.

The member profile(s) database 138 can store data associated with individual members. That is, the member profile(s) database 138 can store data associated with individuals having accounts for accessing services offered by the healthcare management service provider 105. The member profile(s) database 138 can store one or more member profiles respectively corresponding to individual members. A member profile can include member data such as, but not limited to, demographic data of the member (e.g., age, gender, address, occupation, number of children, marital status, etc.), healthcare program data associated with the member (e.g., healthcare program(s) available to the member, claims submitted on behalf of the member, claim authorizations, member engagement with healthcare program(s), etc.), employment records of the member (e.g., employer(s), employment status(es), healthcare program(s) available via the employer(s), etc.), health records of the member (e.g., medical treatments, prescriptions, treatment plans, etc.), etc.

The model(s) database 140 can store model(s) trained by the training module 118. That is, the model(s) database 140 can store model(s) that are trained by the training module 118 such that they are later accessible by the model application module 134 and/or the feedback module 122. Each model can be associated with a particular healthcare application, as described above.

The training data database 142 can store training data that is accessible by the training module 118. Training data can include member data, potential member data, claims data, claim authorizations, etc. As described above, in some examples, the training data can be labeled and in other examples, the training data may not be labeled.

As described above, the data source(s) 102 may send data 108 over one or more networks 106. Network(s) 106 may be any type of network known in the art, such as a local area network or a wide area network, such as the Internet, and may include a wireless network, such as a cellular network, a local wireless network, such as Wi-Fi and/or close-range wireless communications, such as Bluetooth®, BLE, NFC, RFID, a wired network, or any other such network, or any combination thereof. Accordingly, network(s) 106 may include both wired and/or wireless communication technologies, including Bluetooth®, BLE, Wi-Fi and cellular communication technologies, as well as wired or fiber optic technologies. Components used for such communications may depend at least in part upon the type of network, the environment selected, or both. Protocols for communicating over such networks are well known and will not be discussed herein in detail.

Figure 2:
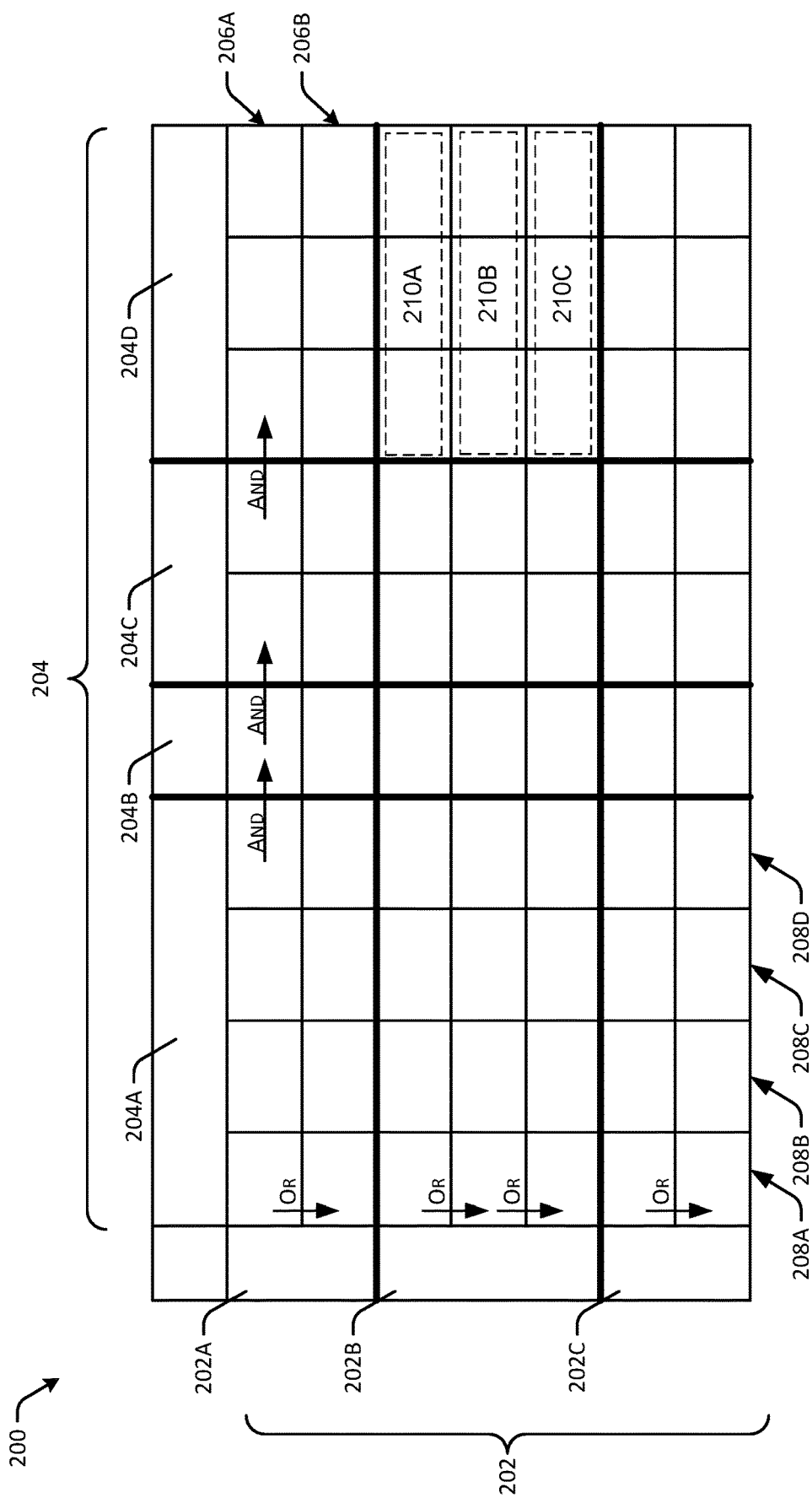
FIG. 2 illustrates an example of a graphical user interface configured for defining a set of rules.

FIG. 2 illustrates an example of a graphical user interface (GUI) 200 configured for defining a set of rules. GUI 200 can be configured in a visual layout of a plurality of row groups 202 and a plurality of column groups 204 (i.e., a spreadsheet). An expert-type user (or a plurality of expert-type users) can specify which attribute(s) they want to search for, as well as the parameters for each attribute. In at least one example, GUI 200 can correspond to a template that an expert-type user can use to define a set of rules. In at least one example, an expert-type user can combine conditions to narrow the scope of their search by moving across the spreadsheet and an expert-type user can broaden the scope of their search by moving down the spreadsheet to encompass additional combinations of parameters.

As described above, GUI 200 can enable individuals having little to no engineering and/or software background to parse information in a data rich environment by providing an accessible user interface to input a set of rules that are associated with a particular healthcare application of interest. That is, GUI 200 enables such expert-type users to manipulate rules and filters without having any prior knowledge of the source code. GUI 200 eliminates, or reduces, the reliance on programmers to serve as intermediaries between individuals interested in extracting data from datasets and the datasets that the expert-type users are interested in evaluating. In at least one example, GUI 200 enables expert-type users to easily and efficiently translate their expertise into logical rules for use in processing data (i.e., via the schema, described above).

As described above, GUI 200 can be configured in a visual layout of a plurality of row groups 202 and a plurality of column groups 204 (i.e., a spreadsheet). As described below, individual rows of a row group and/or individual column groups can be associated with Boolean logic. In at least one example, each row group (e.g., row group 202A, row group 202B, row group 202C) can correspond to a single rule. A rule can correspond to a conditionally independent logical statement that has a binary output (e.g., true or false, etc.). Each row group (e.g., row group 202A, row group 202B, row group 202C) can include one or more rows, for instance row 206A and row 206B, and each of the one or more rows can correspond to a parameter and/or combination of parameters for satisfying a partial condition, described below. To determine that a partial condition is satisfied, the rule set application module 132 can determine that the parameters in one of the rows associated with a row group are true. That is, each of the rows are joined by a logical "OR" and can be associated with disjunctive Boolean logic, as shown in FIG. 2.

In at least one example, a column group (e.g., column group 204A, column group 204B, column group 204C, column group 204D) can correspond to partial condition for satisfying a rule. Each column group (e.g., column group 204A, column group 204B, column group 204C, column group 204D) can include one or more columns, such as column 208A, column 208B, column 208C, and column 208D, and each of the one or more columns can correspond to a parameter of the partial condition. To determine that a partial condition is satisfied, the rule set application module 132 can determine that a one or more parameters associated with a column group are true. To determine that a rule is satisfied, the rule set application module 132 can determine that each partial condition is satisfied. That is, each column group is joined by a logical "AND" and can be associated with conjunctive Boolean logic, as shown in FIG. 2.

In examples where a partial condition is associated with more than one option for satisfying the partial condition (i.e., a row group corresponding to a rule has two or more rows), the rule set application module 132 can determine that the parameters associated with each of the columns in a same row are true to determine that the partial condition is satisfied. For the purpose of this discussion, an option corresponds to all of the parameter(s) in a row of a column group. As an example, a box 210A is shown in association with a first option for satisfying a partial condition corresponding to column group 204D, another box 210B is shown in association with a second option for satisfying a partial condition corresponding to column group 204D, and yet an additional box 210C is shown in association with a third option for satisfying a partial condition corresponding to column group 204D. As described above, if all of the parameter(s) in a row of the column group are determined to be true, the partial condition can be determined to be satisfied. That is, if all three parameters associated with each of the columns in column group 204D are true for the first option (e.g., box 210A), the second option (e.g., box 210B), or the third option (e.g., box 210C), the partial condition corresponding to column group 204D can be determined to be satisfied.

In at least one example, each individual column group (e.g., column group 204A, column group 204B, column group 204C, column group 204D) can be optional. That is, the absence of data associated with a particular partial condition specified in a particular column group can be interpreted as a pass-through and mapped to logical "true" for that particular partial condition. In some examples, a column group can be a housekeeping column group and may not be necessary for satisfying a rule. That is, housekeeping column groups are not conditions to satisfying a rule.

GUI 200 illustrates a spreadsheet whereby an expert-type user can combine conditions to narrow the scope of their search by moving across the spreadsheet and an expert-type user can broaden the scope of their search by moving down the spreadsheet to encompass additional combinations of parameters. However, in alternative examples, an expert-type user can combine conditions to narrow the scope of their search by moving down the spreadsheet and an expert-type user can broaden the scope of their search by moving across the spreadsheet to encompass additional combinations of parameters. That is, in alternative examples, partial conditions can be associated with row groups (instead of column groups) and rules can be associated with column groups (instead of row groups). In such examples, each row in a row group can correspond to a parameter for satisfying the partial condition associated with the row group. Furthermore, each column in a column group can correspond to an option for satisfying the partial condition.

While GUI 200 is displayed as a spreadsheet wherein an expert-type user (or one or more expert-type users) can specify rules, partial conditions, and/or parameters, in additional and/or alternative examples, a GUI can enable an expert-type user (or one or more expert-type users) to specify rules, partial conditions, and/or parameters via drop down menu(s), list(s), free-form text, etc. Furthermore, while the aforementioned description is directed to a GUI, additional and/or alternative user interfaces can be imagined. For instance, in at least one example, an expert-type user can provide speech input, gesture input, etc. to specify rules, partial conditions, and/or parameters.

GUI 200 is one example of an interface that can be utilized to articulate aspects of environment 100. As described above, aspects of environment 100 can be articulated by different users via one or more interfaces. For instance, as described above, an expert-type user, having little to no engineering and/or software background but otherwise having significant knowledge on a particular healthcare application, can input one or more rules via a GUI (e.g., GUI 200). That is the rule(s) 126, as described above can be specific to a particular healthcare application and can be specified by an expert-type user.

Additionally and/or alternatively, the schema can be provided by a power user. In some examples, a power user can be a same user as the expert user and, in other examples, a power user can be a different user than the expert user. In some examples, a power user can have little or no knowledge about a particular healthcare application. The schema, as described above, can be associated with particular domains (e.g., record type, data type, etc.). That is, the schema can be useful for translating different rule(s) that are associated with the same domain. Accordingly, the schema can be utilized across multiple healthcare applications, so long as the multiple healthcare applications are associated with a same domain.

Moreover, programmers can interface with environment 100 so as to program the data processing operations performed by the environment 100. That is, the programmers can provide the instructions for the data processing module 120, which can be generally applicable for the various healthcare applications. The programmers can interface with environment 100 via a different interface than expert-type users and/or power users. In some examples, each user (e.g., power user, expert-type user, programmer) can have different access-control settings, as described above.

FIGS. 3-8 describe example processes for identifying data in a dataset for use in application(s), such as healthcare application(s). The example processes are described in the context of the environment of FIG. 1, but are not limited to that environment. The processes described above in association with FIGS. 3-8 can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functionalities or implement particular abstract data types. In other embodiments, hardware components perform one or more of the operations. Such hardware components can include or be incorporated into processors, application-specific integrated circuits (ASICs), programmable circuits such as field programmable gate arrays (FPGAs), or in other ways. The order in which the operations are described is not intended to be construed as a limitation, and any number of the described operations can be combined in any order and/or in parallel to implement the processes.

Figure 3:
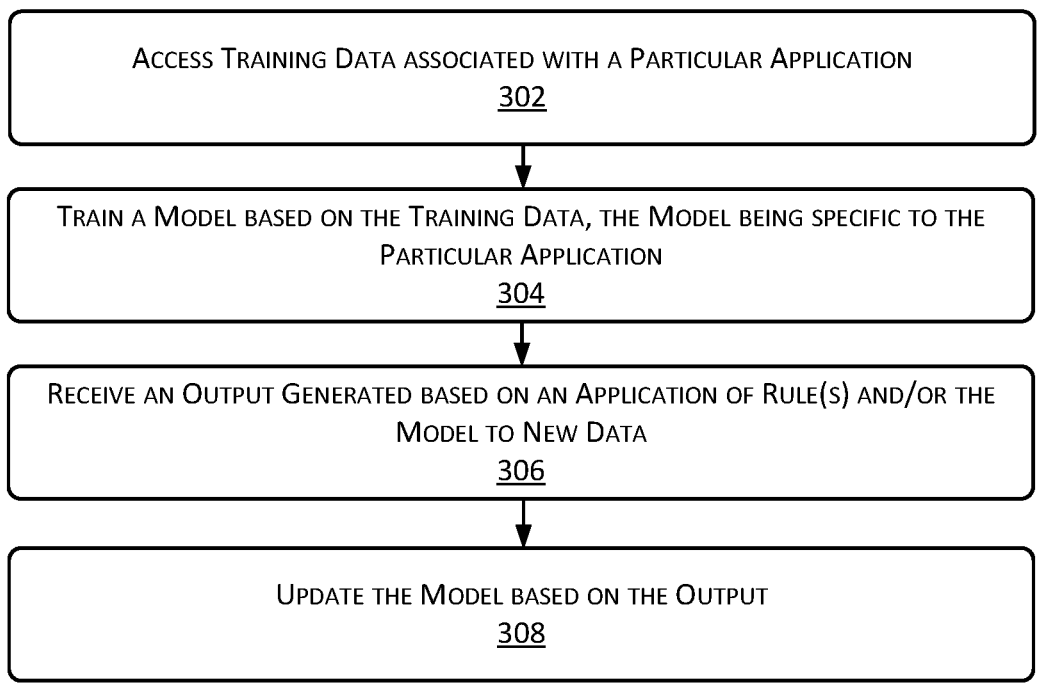
FIG. 3 illustrates an example process for training a model.

FIG. 3 illustrates an example process 300 for training a model that can be utilized for identifying data in a dataset for use in an application, such as a healthcare application.

At operation 302, the training module 118 can access training data associated with a particular application. In at least one example, the particular application may be a healthcare application. As described above, in at least one example, the training module 118 can access a dataset wherein individual data items in the dataset are labeled with a label that corresponds to an outcome associated with the particular healthcare application. The dataset can include member data, potential member data, claim data, data associated with healthcare program(s), etc. For instance, a particular claim that is fraudulent is labeled as being fraudulent. Or, a particular claim that is associated with a mental health classification is labeled as such. In some examples, the training module 118 can access a dataset and can apply a set of rules for labeling individual data items in the dataset. In other examples, the training module 118 can access a dataset that includes previously labeled data items (e.g., manually labeled). In some examples, the training module 118 can access the dataset from the training data 142 in the data store 114.

At operation 304, the training module 118 can train a model based on the training data, the model being specific to the particular application. The training module 118 can be configured to train a model via a machine learning mechanism. A machine learning mechanism can build, modify, or otherwise utilize a model that is created from example inputs and/or associated outputs, and makes predictions or decisions using the model. In at least one example, the model can be trained using supervised learning algorithms, unsupervised learning algorithms, semi-supervised learning algorithms, deep learning algorithms, etc., as described above. In at least one example, the model can be used to predict data items of a dataset that are likely to satisfy an outcome associated with a particular healthcare application.

For instance, the training module 118 can leverage the machine learning mechanism to train a model that identifies individuals that are associated with a particular profile. In such an example, the training module 118 can leverage one or more attributes associated with data corresponding to the individuals and can apply weight(s) to the one or more attributes to determine which attribute(s) of the one or more attributes and/or which weight(s) predict individuals that are associated with the particular profile with a level of accuracy above a predetermined threshold, as described above. Alternatively, in at least one example, the training module 118 can leverage the machine learning mechanism to train a model that identifies individual claims that are likely to be fraudulent. In such an example, the training module 118 can leverage one or more attributes associated with claims and can apply weight(s) to the one or more attributes to determine which attribute(s) of the one or more attributes and/or which weight(s) predict individual claims that are fraudulent at a level of accuracy above a predetermined threshold, as described above. Or, in at least one example, the training module 118 can leverage the machine learning mechanism to train a model that predicts classifications associated with individual claims. In such an example, the training module 118 can leverage one or more attributes associated with claims and can apply weight(s) to the one or more attributes to determine which attribute(s) of the one or more attributes and/or which weight(s) are used to predict respective classifications of individual claims at a level of accuracy above a predetermined threshold, as described above.

At operation 306, the training module 118 can receive an output generated based on an application of rule(s) and/or the model to new data. As described above, the rule set application module 132 can leverage a processed rule set to identify one or more data entries that satisfy the rule set to generate a rules-based output and/or the model application module 134 can apply a model to the one or more data entries to generate a model-based output. The data processing module 120 can access the rules-based output and the model-based output and can combine the rules-based output and the model-based output to generate a combined output. The feedback module 122 can access the combined output.

At operation 308, the training module 118 can update the model based on the output. The feedback module 122 can utilize the combined output to update the model. That is, feedback module 122 can leverage the output of the data processing module 120 (i.e., the combined output) to make adjustments to which attribute(s) and/or weight(s) are used for predicting which data is likely to be of interest in view of a particular healthcare application.

Figure 4:
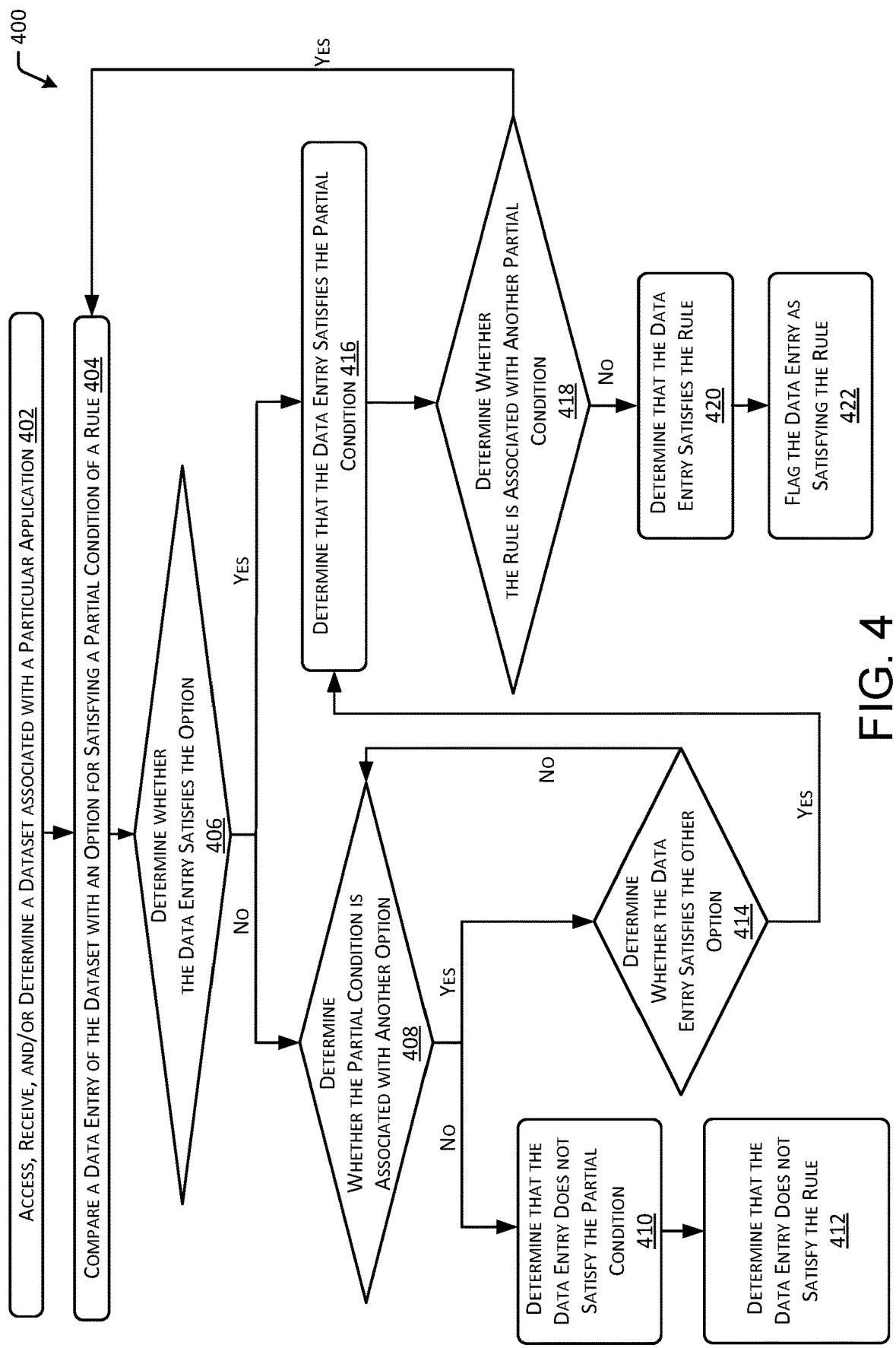
FIG. 4 illustrates an example process for processing data based on a defined set of rules.

FIG. 4 illustrates an example process 400 for processing data based on a defined set of rules. In addition to being described in the context of the environment of FIG. 1, the example process 400 is described in the context of the GUI 200 of FIG. 2, but is not limited to that environment.

At operation 402, the pre-processing module 130 can access, receive, and/or determine a dataset associated with a particular application, such as a particular healthcare application. In at least one example, the pre-processing module 130 can receive data 108 from one or more data sources 102. The data 108 from the one or more data sources 102 can be compiled into a dataset for processing. In at least one example, the pre-processing module 130 can access data from the data store 414 and can aggregate data from the data store 114 with data 108 received from the one or more data sources 102. The aggregated data can include member data, potential member data, claim data, data associated with healthcare program(s), data associated with service(s) available via the healthcare management service provider 105, etc. The data in the dataset may vary depending on which particular healthcare application is applicable to process 400.

In at least one example, the pre-processing module 130 can convert data items in the dataset into digestible data using a predefined programming language (e.g., python, R, C, C++, Java, SparkQL, etc.). For instance, in some examples, the pre-processing module 130 can arrange data 108 from the data source(s) 102 and/or data from the data store 114 in a tabular format. In such examples, individual rows of a table can represent individual data entries. Depending on the particular healthcare application, a data entry can correspond to a data entry associated with an individual (e.g., a member, a potential member, etc.), a claim, etc. That is, the pre-processing module 130 can arrange data 108 from the data source(s) 102 and/or data from the data store 114 in a tabular format such that a plurality of data entries associated with individuals (e.g., member(s), potential member(s), etc.), a plurality of claims, etc. can be processed via the processes described below. As described above, additionally and/or alternatively, the pre-processing module 130 can arrange data 108 from the data source(s) 102 into a non-tabular format, such as a serialized object format in various markup languages (e.g., JSON, yaml, etc.). In some examples, the pre-processing module 130 can apply filters to a dataset to eliminate portions (e.g., column(s), row(s), etc.) that are not relevant to a particular search. In some examples, the pre-processing module 130 can append one or more features to the data items in the dataset, as described above.

At operation 404, the rule set application module 132 can compare a data entry of the data set with an option for satisfying a partial condition of a rule. The rule set application module 132 can apply the rule(s) 126 to the dataset by applying a corresponding processed rule set to the dataset. In at least one example, the rule set application module 132 applies each rule of the processed rule set to individual data entries in the dataset to determine whether each data entry satisfies the rule. That is, in at least one example, the rule set application module 132 calls a function corresponding to a particular rule and, responsive to making the call for the function, evaluates a data entry using the particular rule. As described above with reference to FIG. 2, each rule can correspond to an attribute of interest to a particular healthcare application. Additionally, each rule can be associated with one or more partial conditions. Each partial condition can be associated with one or more parameters for satisfying the partial condition. As described above, a parameter can correspond to a column of a column group. Each rule can be associated with one or more options for satisfying a partial condition. As described above, an option can correspond to a row of a row group. That is, an option can correspond to one or more parameters associated with a row of a row group. In at least one example, the rule set application module 132 can compare a data entry of the data set with one or more parameters of an option to determine whether the data entry satisfies the option.

At operation 406, the rule set application module 132 can determine whether the data entry satisfies the option. Based at least in part on comparing the data entry with the one or more parameters of an option, the rule set application module 132 can determine whether the data entry satisfies the option. That is, the rule set application module 132 can determine whether the data entry makes the option true.

Based at least in part on determining that the data entry does not satisfy the option, the rule set application module 132 can determine whether the partial condition is associated with another option, as illustrated at operation 408. As described above, a partial condition can be associated with one or more options (e.g., one or more rows) for satisfying the partial condition. Accordingly, based at least in part on determining that the data entry does not satisfy the option, the rule set application module 132 can determine whether the partial condition is associated with another option. That is, the rule set application module 132 can determine whether the partial condition is associated with another row of parameters for satisfying the partial condition.

Based at least in part on determining that the partial condition is not associated with another option, the rule set application module 132 can determine that the data entry does not satisfy the partial condition, as illustrated at operation 410, and that the data entry does not satisfy the rule, as illustrated at operation 412. Based at least in part on determining that the partial condition is associated with another option, the rule set application module 132 can determine whether the data entry satisfies the other option, as illustrated at operation 414. Based at least in part on determining that the data entry does not satisfy the other option, the rule set application module 132 can return to operation 408 to determine whether the partial condition is associated with yet another option. Based at least in part on determining that the data entry satisfies the other option, the rule set application module 132 can determine that the entry satisfies the partial condition, as illustrated at operation 416.

At operation 416, the rule set application module 132 can determine that the data entry satisfies the partial condition. In at least one example, based at least in part on the rule set application module 132 determining that the data entry satisfies the option (e.g., a "yes" output from operation 406), the rule set application module 132 can determine that the data entry satisfies the option. Alternatively, based at least in part on determining that the data entry satisfies the other option (e.g., a "yes" output from operation 414), the rule set application module 132 can determine that the entry satisfies the partial condition.

At operation 418, the rule set application module 132 can determine whether the rule is associated with another partial condition. If the rule set application module 132 determines that the rule is not associated with any other partial conditions, the rule set application module 132 can determine that the data entry satisfies the rule, as illustrated at operation 420. In at least one example, the rule set application module 132 can flag the data entry as satisfying the rule, as illustrated at operation 422.

Based at least in part on determining that the rule is associated with another partial condition, the rule set application module 132 can return to block 404 to determine whether the data entry satisfies an option associated with the other partial condition. That is, the rule set application module 132 can repeat relevant operations 404-416 to determine whether the data entry satisfies the other partial condition. Based at least in part on determining that the data entry satisfies each partial condition associated with a rule, the rule set application module 132 can determine that the data entry satisfies the rule, as illustrated at operation 420. In an example where a rule is associated with more than one partial condition, the rule set application module 132 can determine that the data entry satisfies the rule so long as each partial condition is satisfied without regard to which option (i.e., which row of a row group) was used to satisfy each of the partial conditions. Based at least in part on determining that the data entry does not satisfy the other partial condition, the rule set application module 132 can determine that the data entry does not satisfy the rule, as illustrated at operation 412.

As described above, a particular healthcare application can be associated with a set of rules, which can correspond to one or more rules. In such examples, the rule set application module 132 can repeat process 400 until the rule set application module determines whether the data entry satisfies each rule of the set of rules. In some examples, the rule set application module 132 can flag the data entry to indicate that the data entry satisfies a particular rule of the set of rules, as illustrated at operation 422. In other examples, the rule set application module 132 can refrain from flagging the data entry until the rule set application module 132 determines that the data entry satisfies all rules of the set of rules.

Figure 5:
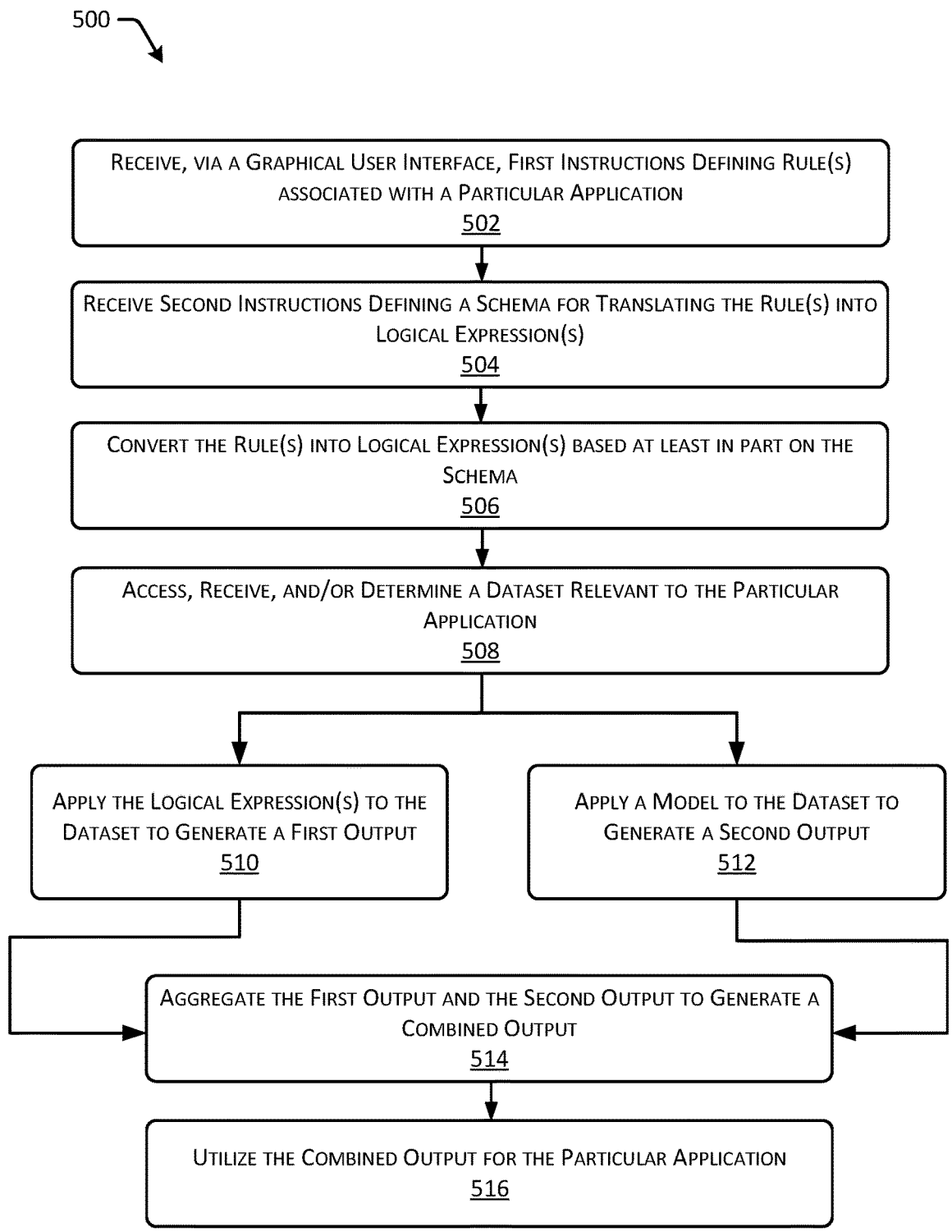
FIG. 5 illustrates an example process for applying logical expressions generated from a predefined set of rules and/or a model to a set of data relevant to a particular application to generate an output for use with the particular application.

FIG. 5 illustrates an example process 500 for applying logical expressions generated from a predefined set of rules and/or a model to a set of data relevant to a particular application to generate an output for use with the particular application.

At operation 502, the rule set application module 132 can receive, via a graphical user interface (GUI), first instructions defining rule(s) associated with a particular application. In at least one example, the particular application may be associated with a healthcare application. In at least one example, the rule(s) 126 can be articulated by an expert-type user via a GUI, an example of which is shown and described above with reference to FIG. 2. In some examples, multiple expert-type users can input rules via the GUI at substantially the same time via different devices operated by the multiple expert-type users, which may be remotely located. That is, in some examples, the GUI can enable collaborative and/or distributed entry of rules.

In at least one example, the rule(s) 126 can be associated with a particular healthcare application. That is, the rule(s) 126 can be defined by one or more expert-type users such that the data processing module 120 can leverage the rule(s) 126 to filter a dataset and identify data that is relevant to the particular healthcare application. In some examples, the rule(s) can be leveraged to perform a search over a dataset to identify data that is relevant to the particular healthcare application. For instance, one or more expert-type users can desire to identify individuals (e.g., members and/or potential members) that are associated with a profile. In such an example, the rule(s) 126 can be associated with attribute(s) of the profile. Additionally and/or alternatively, one or more expert-type users can desire to identify fraudulent claims. In such an example, the rule(s) 126 can be associated with attribute(s) of a fraudulent claim. Or, one or more expert-type users can be interested in classifying claims. In such an example, the rule(s) can be associated with attribute(s) of a particular classification of a claim.

Table 2 is provided below, illustrates a rule of a set of rules input into the GUI. The rule includes three partial conditions. A first partial condition is associated with a Current Procedural Terminology (CPT) code and includes three parameters: CPT_from, CPT_to, and CPT_include. A second partial condition is associated with age and includes two parameters: Age_from and Age to. A third partial condition is associated with a POS and includes one parameter: POS_code. Values for satisfying the parameters are specified in Table 2. Additionally, Table 2 includes one row group (Row Group 1), which includes three rows. Each row, as described above, can provide an option for satisfying the partial condition. Table 2 is for illustrative purposes only and should not be construed as limiting.

TABLE 2

| | | CPT Code | | | Age | | Place of Service (POS) |
|---|---|---|---|---|---|---|---|
| | | CPT_from | CPT_to | CPT_incl | Age_from | Age_to | POS_code |
| Row Group 1 | R001 | 70010 | 70015 | Include | 21 | 45 | 12 |
| | R001 | 70151 | 70151 | Include | | | 11 |
| | R001 | 70180 | 70190 | Include | | | |

At operation 504, the rule set generation module 116 can receive second instructions defining a schema for translating the rule(s) into logical expression(s). In addition to receiving the rule(s) 126, the rule set generation module 116 can receive schema 128. In at least one example, the schema 128 can translate the rule(s) 126 into logical expression(s) which can be used by the data processing module 120 to process datasets. In at least one example, the schema 128 can be provided by a power user, as described above. A non-limiting example of a schema corresponding to the rule illustrated in Table 2 is provided below with reference to Table 3. Table 3 is for illustrative purposes only and should not be construed as limiting.

TABLE 3

| Name | Group | Group Type | Element Name | Element Type | Function to Apply |
|---|---|---|---|---|---|
| CPT_from | CPT | key_value_map | cpt_from | cpt | within_code_range |
| CPT_to | CPT | key_value_map | cpt_to | cpt | within_code_range |
| CPT_incl | CPT | key_value_map | include_or_exclude | string | within_code_range |
| Age_from | Age | key_value_map | age_from | age | within_age_range |
| Age_to | Age | key_value_map | age_to | age | within_age_range |
| POS_code | POS | list | pos_code | pos | equals |

At operation 506, the rule set generation module 116 can convert the rule(s) into logical expression(s) based at last in part on the schema. That is, the rule set generation module 116 can translate each rule 126 into a logical expression based on definitions that exist in the schema 128. Based at least in part on applying the schema 128 to the rule(s) 126, the rule set generation module 116 can store a resulting rule set in a machine-readable format in the data store 114. That is, as described above, the rule set generation module 116 can convert the user-editable rule(s) into computer-executable logical expression(s) using the schema 128.

In some examples, the rule set generation module 116 can process the rule(s) 126 using a set of pre-defined criteria to determine the validity of the rule(s) 126 prior to applying the schema 128 to the rule(s) 126. For instance, the rule set generation module 116 can determine that the rule(s) 126 are input in a datatype that can be processed via schema 128. Additionally, in at least one example, the rule set generation module 116 can bind a function to each rule of a rule set. The data processing module 120 can call the function to run the corresponding rule against a dataset. In some examples, prior to binding the function to each rule of the rule set, the rule set generation module 116 can perform a rule validation check so that each rule is in an expected format such that the data processing module 120 can call the proper function for applying a rule to a dataset. A function that is bound to a rule can be stored with the corresponding rule in the data store 114. The processed rule set can be stored in a machine-readable format in the data store 114.

At operation 508, the rule set generation module 116 can access, receive, and/or determine a dataset relevant to the particular application. In at least one example, the pre-processing module 130 can receive data 108 from one or more data sources 102. The data 108 from the one or more data sources 102 can be compiled into a dataset for processing. In at least one example, the pre-processing module 130 can access data from the data store 414 and can aggregate data from the data store 114 with data 108 received from the one or more data sources 102. The aggregated data can include member data, potential member data, claims data, data associated with healthcare program(s), data associated with service(s) available via the healthcare management service, etc. The contents of the dataset may vary depending on the particular application.

In at least one example, the pre-processing module 130 can convert data items in the dataset into digestible data using a predefined programming language (e.g., python, R, C, C++, Java, SparkQL, etc.). For instance, in some examples, the pre-processing module 130 can arrange data 108 from the data source(s) 102 and/or data from the data store 114 in a tabular format. In such examples, individual rows of a table can represent individual data entries. Depending on the particular application, a data entry can correspond to a data entry associated with an individual (e.g., a member, a potential member, etc.), a claim, etc. That is, the pre-processing module 130 can arrange data 108 from the data source(s) 102 and/or data from the data store 114 in a tabular format such that a plurality of data entries associated with individuals (e.g., members, potential members, etc.), a plurality of claims, etc. can be processed via the processes described below. In some examples, the pre-processing module 130 can apply filters to a dataset to eliminate portions (e.g., column(s), row(s), etc.) that are not relevant to a particular search. As described above, additionally and/or alternatively, the pre-processing module 130 can arrange data 108 from the data source(s) 102 into a non-tabular format, such as a serialized object format in various markup languages (e.g., JSON, yaml, etc.). In some examples, the pre-processing module 130 can append one or more features to the data items in the dataset. In at least one example, the one or more features can be calculations based on existing data items (e.g., the time between two dates associated with data item(s)).

Table 4, below, is a non-limiting example of a dataset. As a non-limiting example, each claim_id can correspond to a data entry as described herein.

TABLE 4

| Claim_id | CPT | Age | Place of Service (POS) |
|---|---|---|---|
| 1 | 15297 | 35 | 11 |
| 2 | 70185 | 23 | 81 |
| 3 | 70012 | 42 | 12 |

At operation 510, the rule set generation module 116 can apply the logical expression(s) to the dataset to generate a first output. The rule set application module 132 can apply the rule(s) 126 to the dataset by applying a corresponding processed rule set to the dataset. In at least one example, the rule set application module 132 applies each rule of the processed rule set to individual data entries in the tabularly formatted dataset to determine whether each data entry satisfies the rule. That is, in at least one example, the rule set application module 132 calls a function corresponding to a particular rule and, responsive to making the call for the function, evaluates a data entry using the particular rule. As an example, the rule set application module 132 can call a function associated with a particular rule and can apply the particular rule to a claim to determine whether the claim satisfies the particular rule. Or, the rule set application module 132 can call a function associated with a particular rule and apply the particular rule to member data associated with a member (e.g., in a member profile, described below) to determine whether the member data satisfies the particular rule.

The rule set application module 132 can repeat the aforementioned process for each rule in the rule(s) 126. That is, the rule set application module 132 can apply each rule in the rule(s) 126 to a data entry to determine whether the data entry satisfies all of the rule(s) 126. Based at least in part on determining that a data entry of the dataset satisfies rule(s) 126, the rule set application module 132 can flag the data entry. The rule set application module 132 can repeat the aforementioned process for each data entry in a dataset. Flagged data entries can be identified in an output of the rule set application module 132. That is, a rules-based output can identify one or more flagged data items. Additional details associated with applying the rule(s) 126 to the dataset are described above with reference to FIG. 4.

As a non-limiting example, the rule set application module 132 can apply the rule illustrated above in TABLE 2 to a first data entry in TABLE 4. That is, the rule set application module 132 can apply the rule illustrated above in TABLE 2 to Claim_id 1. Based at least in part on applying the rules illustrated above in TABLE 2 to Claim_id 1, the rule set application module 132 can determine that Claim_id 1 does not satisfy the rule. That is, because the CPT code is not within one of the CPT code ranges provided, Claim_id 1 does not satisfy the rule. Then, the rule set application module 132 can apply the rule illustrated above in TABLE 2 to Claim_id 2. Based at least in part on applying the rules illustrated above in TABLE 2 to Claim_id 2, the rule set application module 132 can determine that Claim_id 2 does not satisfy the rule. That is, because the place of service code associated with Claim_id 2 is not one of the place of service codes provided, Claim_id 2 does not satisfy the rule. Further, the rule set application module 132 can apply the rule illustrated above in TABLE 2 to Claim_id 3. Based at least in part on applying the rules illustrated above in TABLE 2 to Claim_id 3, the rule set application module 132 can determine that Claim_id 3 satisfies the rule. That is, because the CPT code is within one of the CPT code ranges provided, the age is within the age range provided, and the place of service code is one of the place of service codes provided, Claim_id 3 satisfies the rule.

TABLE 5 is provided below to illustrate the output of applying the rule illustrated above in TABLE 2 to the dataset represented in TABLE 4. TABLE 5 is provided for illustrative purposes and should not be construed as limiting.

TABLE 5

| Claim_id | CPT | Age | Place of Service (POS) | Satisfies Rule? |
|---|---|---|---|---|
| 1 | 15297 | 35 | 11 | NO |
| 2 | 70185 | 23 | 81 | NO |
| 3 | 70012 | 42 | 12 | YES |

At operation 512, the model application module 134 can apply a model to the dataset to generate a second output. As described above, the training module 118 can train a model via a machine learning mechanism, as described above with reference to FIG. 3. As described above, the model(s) database 140 associated with the data store 114 can store model(s) that are trained by the training module 118 such that they are later accessible by the model application module 134. Each model can be associated with a particular application, such as a particular healthcare application, as described above. Based at least in part on determining which particular healthcare application is applicable, the model application module 134 can access a corresponding model and can apply the model to the dataset.

In at least one example, the rule set application module 132 and the model application module 134 can process the dataset in parallel (i.e., at substantially the same time). The model application module 134 can identify one or more data entries in the dataset that are likely to be of interest in view of a particular healthcare application. In some examples, the model application module 134 can output a confidence score in association with a data entry of the one or more data entries. In at least one example, the model application module 134 can flag the one or more data entries that are determined to likely be of interest in view of the particular healthcare application. In an additional and/or alternative example, the model application module 134 can flag data entry(s) that are associated with confidence values above a threshold value, in a predetermined range of confidence values, etc. The output of the model application module 134 can be a model-based output. That is, the model-based output can include one or more flagged data entries. In some examples, the one or more flagged data entries can be associated with respectively corresponding confidence values.

At operation 514, the data processing module 120 can aggregate the first output and the second output to generate a combined output. The data processing module 120 can access the rules-based output and the model-based output and can combine the rules-based output and the model-based output. In some examples, the rules-based output and the model-based output can be associated with the same flagged data entry(s). In other examples, the rules-based output and the model-based output can be associated with one or more different flagged data entry(s). In such examples, the model-based output can supplement the rules-based output. In at least one example, the data processing module 120 can compare the rules-based output and the model-based output to determine duplicative flagged data entry(s). The data processing module 120 can eliminate one of the duplicative flagged data entry(s) so that the combined output does not include duplicative flagged data entry(s). Additionally and/or alternatively, the data processing module 120 can leverage conflict resolution policies to resolve conflicts between the rules-based output and the model-based output. That is, in some examples, the data processing module 120 can leverage one or more conflict resolution policies to prioritize the rules-based output over the model-based output or vice versa. In at least one example, the data processing module 120 can apply probabilistic fusion and/or other conditions, which can be integrated into the conflict resolution policies.

At operation 516, the application module 124 can utilize the combined output for the particular application. In at least one example, the application module 124 can access the output of the data processing module 120 (e.g., the rules-based output and the model-based output) and can utilize the output for a particular healthcare application. As described above, the output can be used for healthcare applications such as, but not limited to, healthcare program navigation and/or management, fraud detection, claim mapping, validation, and/or routing, auditing, search strategies, etc., as described herein.

Figure 6:
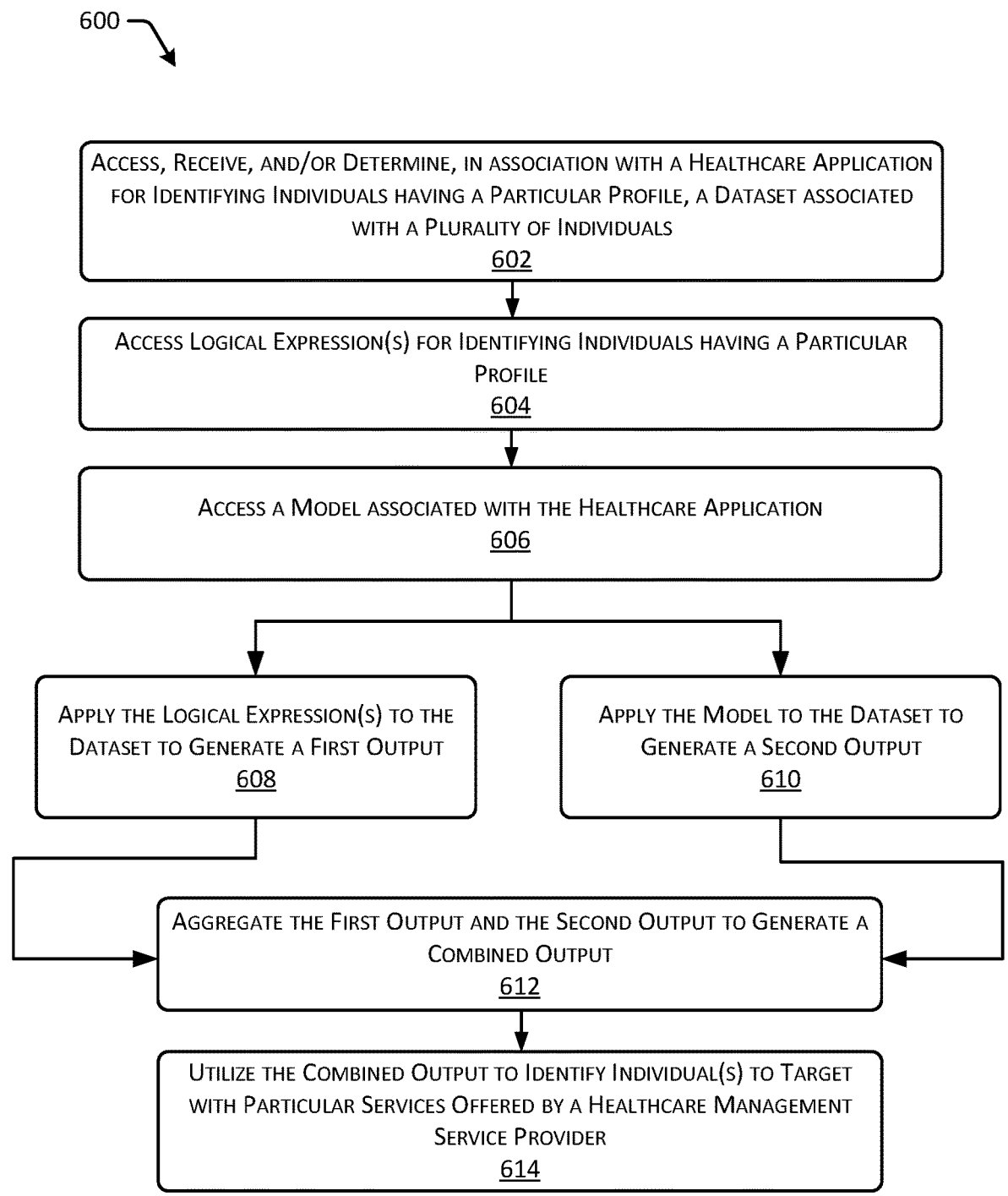
FIG. 6 illustrates an example process for applying logical expressions generated from a predefined set of rules and/or a model to a set of data relevant to a healthcare application for identifying individuals to offer services provided by a healthcare management service provider.

FIG. 6 illustrates an example process 600 for applying logical expressions generated from a predefined set of rules and/or a model to a set of data relevant to a healthcare application for identifying individuals to offer services provided by a healthcare management service provider.

At operation 602, the rule set generation module 116 can access, receive, and/or determine, in association with a healthcare application for identifying individuals having a particular profile, a dataset associated with a plurality of individuals. As described above, in at least one example, the healthcare management service provider 105 can leverage the techniques described herein to identify individuals who may benefit from a particular service offered by the healthcare management service provider 105 (e.g., target members). In some examples, the individuals can be members of the healthcare management service provider 105. That is, the individuals have an account through which the individuals can access services offered by the healthcare management service provider 105. In additional and/or alternative examples, the individuals can be potential members. That is, the individuals may not have an account through which the individuals can access services offered by the healthcare management service provider 105, but can benefit from a particular service offered by the healthcare management service provider 105. In such an example, the relevant data may include data entries associated with individuals (e.g., members, potential members, etc.).

In at least one example, the pre-processing module 130 can receive data 108 associated with individuals from one or more data sources 102. The data 108 from the one or more data sources 102 can be compiled into a dataset for processing. In at least one example, the pre-processing module 130 can access data from the data store 414, for instance from the member profile(s) 138. In some examples, the pre-processing module 130 can aggregate data from the data store 114 with data 108 received from the one or more data sources 102. The data 108 can include data indicating claims associated with individuals, healthcare program authorizations associated with individuals, healthcare program utilization by individuals, engagement of individuals, preferences of individuals, medical data associated with individuals, etc. In at least one example, the pre-processing module 130 can convert data items in the dataset into digestible data using a predefined programming language (e.g., python, R, C, C++, Java, SparkQL, etc.), as described above.

At operation 604, the rule set application module 132 can access logical expression(s) for identifying individuals having a particular profile. That is, the rule set application module 132 can access the rule set(s) 136 in the data store 114 and access a rule set that is applicable for a healthcare application for identifying individuals having a particular profile. In at least one example, the set of rules can identify attributes of a particular (i.e., target) profile. For instance, the particular profile can correspond to a profile of one or more individuals that would benefit from particular program(s) and/or resource(s) offered by the healthcare management service provider 105.

At operation 606, the model application module 134 can access a model associated with the healthcare application. That is, in at least one example, the model application module 134 can access the model(s) 140 in the data store 114 and access a model that is applicable for the healthcare application. That is, the rule set application module 132 can access the model(s) 140 in the data store 114 and access a model that is applicable for a healthcare application for identifying individuals having a particular profile.

At operation 608, the rule set application module 132 can apply the logical expression(s) to the data set to generate a first output. The first output can correspond to one or more individuals that match the particular profile. That is, the one or more individuals can have attributes corresponding to the attributes identified by the particular profile. At substantially the same time, at operation 610, the model application module 134 can apply the model to the dataset to generate a second output. The second output can correspond to one or more individuals predicted to match the particular profile.

At operation 612, the data processing module 120 can aggregate the first output and the second output to generate a combined output. The data processing module 120 can access the rules-based output and the model-based output and can combine the rules-based output and the model-based output. In some examples, the rules-based output and the model-based output can be associated with the same individuals. In other examples, the rules-based output and the model-based output can be associated with one or more different individuals. In such examples, the model-based output can supplement the rules-based output. In at least one example, the data processing module 120 can compare the rules-based output and the model-based output to determine when an individual is associated with both outputs and can eliminate one instance of the individual in the aggregated output. Additionally and/or alternatively, the data processing module 120 can leverage conflict resolution policies to resolve conflicts between the rules-based output and the model-based output, as described above.

At operation 614, the application module 124 can utilize the combined output to identify individual(s) to target with particular services offered by a healthcare management service provider 105. As described above, the application module 124 can leverage various tools to connect identified individuals to particular program(s) and facilitate relevant engagement so that the identified individuals are able to take advantage of services that are available via the healthcare management service provider 105. For instance, in at least one example, the application module 124 can send and/or provide various communications to individuals identified via the aggregated output. For instance, the application module 124 can send emails, text messages, and/or push notifications to individuals identified via the aggregated output, send messages to individuals identified via the aggregated output via a website portal and/or an application, call individuals identified via the aggregated output, etc. In some examples, the communications can guide the individuals through complex programs, resolutions of healthcare claim benefit issues, and/or management of certain health characteristics. Additionally and/or alternatively, the application module 124 can generate a recommendation for individuals identified in the aggregated output. The recommendation can include product partners, unknown (to the individual(s)) healthcare program benefits, healthcare program design incentives, etc. Moreover, the application module 124 can determine and recommend healthcare program changes to an employer and/or employers associated with individuals identified via the rules-based output and/or the model-based output.

Figure 7:
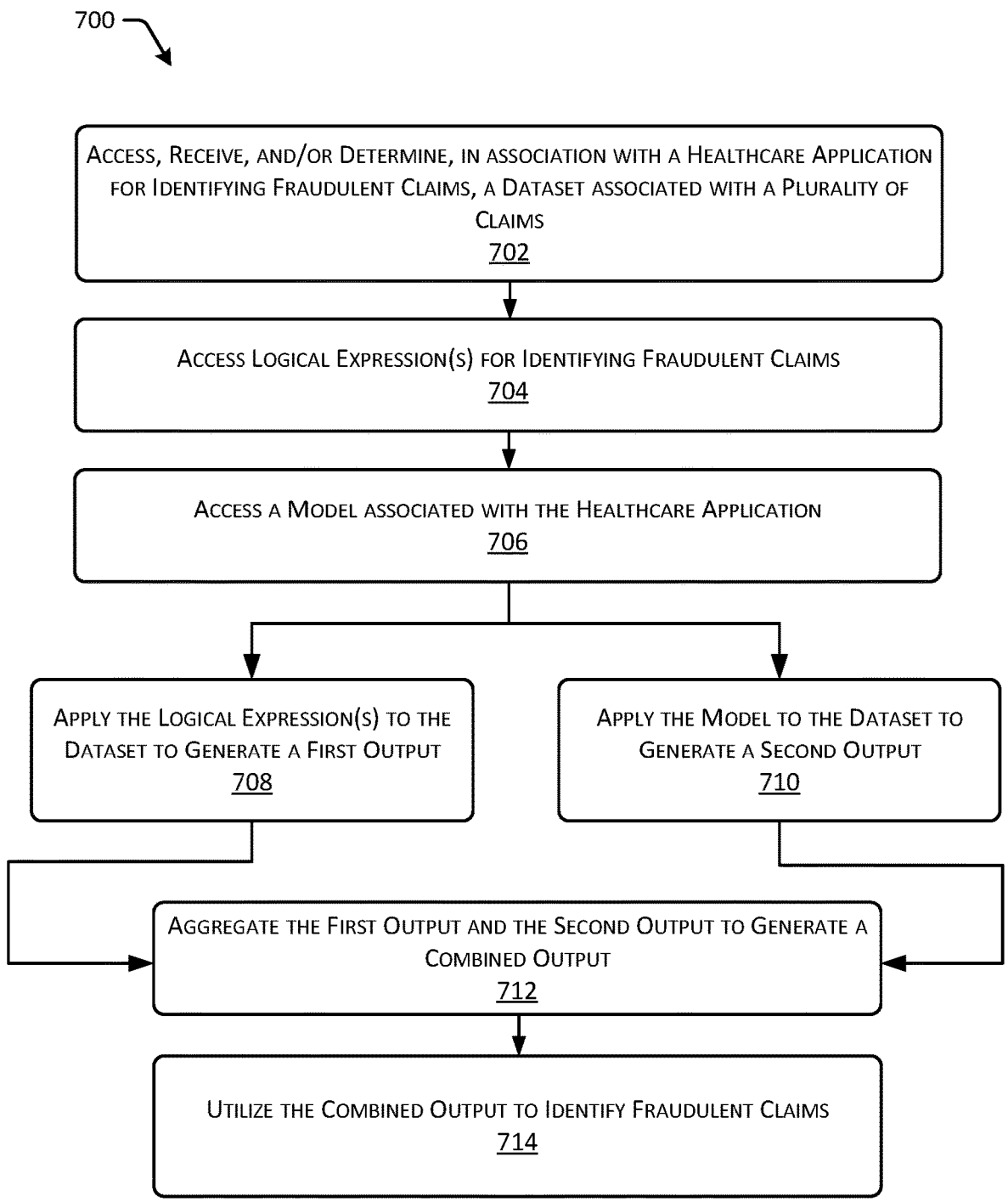
FIG. 7 illustrates an example process for applying logical expressions generated from a predefined set of rules and/or a model to a set of data relevant to a healthcare application for identifying fraudulent claims.

FIG. 7 illustrates an example process 700 for applying logical expressions generated from a predefined set of rules and/or a model to a set of data relevant to a healthcare application for identifying fraudulent claims.

At operation 702, the rule set generation module 116 can access, receive, and/or determine, in association with a healthcare application for identifying fraudulent claims, a dataset associated with a plurality of claims. As described above, a healthcare application can be directed to analyzing claims data to determine whether claims are fraudulent. In such examples, the relevant dataset may include claims. As described above, a claim can identify an individual who received a service, the service provided, a service provider that provided the service, a date associated with the service, a time associated with the service, a location associated with the service, a cost associated with the service, a code associated with the service, etc. In at least one example, the pre-processing module 130 can receive data 108 (e.g., the claims) from one or more data sources 102. The data 108 from the one or more data sources 102 can be compiled into a dataset for processing. In at least one example, the pre-processing module 130 can access data from the data store 414. In some examples, the pre-processing module 130 can aggregate data from the data store 114 with data 108 received from the one or more data sources 102. In at least one example, the pre-processing module 130 can convert data items in the dataset into digestible data using a pre-defined programming language (e.g., python, R, C, C++, Java, SparkQL, etc.), as described above.

At operation 704, the rule set application module 132 can access logical expression(s) for identifying fraudulent claims. That is, in at least one example, the rule set application module 132 can access the rule set(s) 136 in the data store 114 and access a rule set that is applicable for the healthcare application. That is, the rule set application module 132 can access the rule set(s) 136 in the data store 114 and access a rule set that is applicable for a healthcare application for identifying fraudulent claims. In at least one example, the set of rules can identify attributes of a fraudulent claim.

At operation 706, the model application module 134 can access a model associated with the healthcare application. That is, in at least one example, the model application module 134 can access the model(s) 140 in the data store 114 and access a model that is applicable for the healthcare application. That is, the rule set application module 132 can access the model(s) 140 in the data store 114 and access a model that is applicable for a healthcare application for identifying fraudulent claims.

At operation 708, the rule set application module 132 can apply the logical expression(s) to the data set to generate a first output. The first output can correspond to one or more claims identified to be fraudulent. At substantially the same time, at operation 710, the model application module 134 can apply the model to the dataset to generate a second output. The second output can correspond to one or more claims predicted to be fraudulent.

At operation 712, the data processing module 120 can aggregate the first output and the second output to generate a combined output. The data processing module 120 can access the rules-based output and the model-based output and can combine the rules-based output and the model-based output. In some examples, the rules-based output and the model-based output can be associated with the same claims. In other examples, the rules-based output and the model-based output can be associated with one or more different claims. In such examples, the model-based output can supplement the rules-based output. In at least one example, the data processing module 120 can compare the rules-based output and the model-based output to determine when a claim is associated with both outputs and can eliminate one instance of the claim in the aggregated output. Additionally and/or alternatively, the data processing module 120 can leverage conflict resolution policies to resolve conflicts between the rules-based output and the model-based output, as described above.

At operation 714, the application module 124 can utilize the combined output to identify fraudulent claims. In at least one example, based on identifying fraudulent claims, the application module 124 can flag the fraudulent claims for further review by a computing system and/or human analyst.

Figure 8:
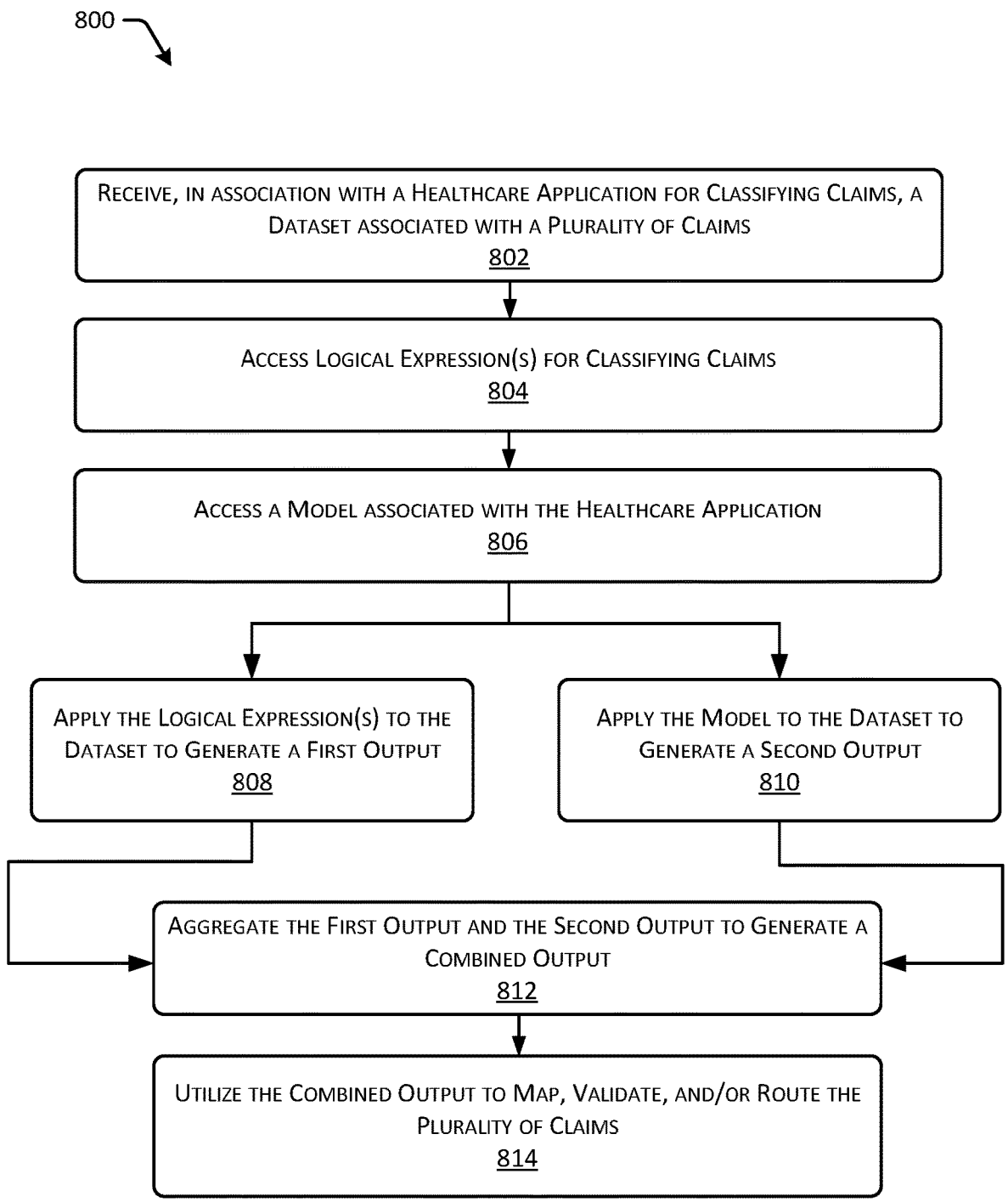
FIG. 8 illustrates an example process for applying logical expressions generated from a predefined set of rules and/or a model to a set of data relevant to a healthcare application for classifying claims.

FIG. 8 illustrates an example process 800 for applying logical expressions generated from a predefined set of rules and/or a model to a set of data relevant to a healthcare application for classifying claims.

At operation 802, the rule set generation module 116 can access, receive, and/or determine, in association with a healthcare application for classifying claims, a dataset associated with a plurality of claims. As described above, a healthcare application can be directed to analyzing claims data for claim mapping, validation, and/or routing, or making other observations based on claims data. In such examples, the relevant dataset may include claims. In at least one example, the pre-processing module 130 can receive data 108 from one or more data sources 102. The data 108 from the one or more data sources 102 can be compiled into a dataset for processing. In at least one example, the pre-processing module 130 can access data from the data store 414. In some examples, the pre-processing module 130 can aggregate data from the data store 114 with data 108 received from the one or more data sources 102. In at least one example, the pre-processing module 130 can convert data items in the dataset into digestible data using a pre-defined programming language (e.g., python, R, C, C++, Java, SparkQL, etc.), as described above.

At operation 804, the rule set application module 132 can access logical expression(s) for classifying claims. That is, in at least one example, the rule set application module 132 can access the rule set(s) 136 in the data store 114 and access a rule set that is applicable for the healthcare application. That is, the rule set application module 132 can access the rule set(s) 136 in the data store 114 and access a rule set that is applicable for a healthcare application for classifying claims. In at least one example, the set of rules can identify attributes of particular class(es) of claims.

At operation 806, the model application module 134 can access a model associated with the healthcare application. That is, in at least one example, the model application module 134 can access the model(s) 140 in the data store 114 and access a model that is applicable for the healthcare application. That is, the rule set application module 132 can access the model(s) 140 in the data store 114 and access a model that is applicable for a healthcare application for classifying claims.

At operation 808, the rule set application module 132 can apply the logical expression(s) to the data set to generate a first output. The first output can correspond to one or more claims that are associated with a particular class. At substantially the same time, at operation 810, the model application module 134 can apply the model to the dataset to generate a second output. The second output can correspond to a prediction of one or more claims that are associated with the particular class.

At operation 812, the data processing module 120 can aggregate the first output and the second output to generate a combined output. The data processing module 120 can access the rules-based output and the model-based output and can combine the rules-based output and the model-based output. In some examples, the rules-based output and the model-based output can be associated with the same claims. In other examples, the rules-based output and the model-based output can be associated with one or more different claims. In such examples, the model-based output can supplement the rules-based output. In at least one example, the data processing module 120 can compare the rules-based output and the model-based output to determine when a claim is associated with both outputs and can eliminate one instance of the claim in the aggregated output. Additionally and/or alternatively, the data processing module 120 can leverage conflict resolution policies to resolve conflicts between the rules-based output and the model-based output, as described above.

At operation 614, the application module 124 can utilize the combined output to map, validate, and/or route the plurality of claims. For instance, the application module 124 can use the aggregated output to classify claims, map claims to particular classifications, validate previous classifications of claims, etc., depending on the relevant healthcare application. In at least one example, claim classification may be useful for grouping claims by events and/or episodes. In at an additional and/or alternative example, claim classification can be useful for initiating an adjudication process to adjudicate claims based on respective classifications. That is, in at least one example, the application module 124 can be useful for value-based care applications.

As described above, there are various additional and/or alternative uses for the techniques described above. In some examples, the application module 124 can utilize aggregated output for auditing purposes. For instance, the application module 124 can utilize aggregated output for verifying and auditing healthcare data sources and/or healthcare reporting data. Furthermore, the application module 124 can utilize aggregated output for implementing search strategies. For instance, the application module 124 can leverage a classified data entry to retrieve related information corresponding to the data entry. For instance, based at least in part on classifying a support ticket (e.g., a request for support) with a particular class, additional information for responding to such a support ticket can be accessed via a search using the particular class. Or, based at least in part on classifying a benefit with a particular benefit class, additional information for describing the benefit can be accessed via a search using the particular class.

Furthermore, techniques described herein are described in the context of healthcare applications. However, techniques described herein are not limited to such applications. For instance, techniques described herein may be directed to a variety of application(s) that utilize expert systems to identify relevant information.

Although the subject matter has been described in language specific to structural data items and/or methodological acts, it is to be understood that the subject matter defined in the appended claims is not necessarily limited to the specific data items or acts described. Rather, the specific data items and acts are disclosed as exemplary forms of implementing the claims.

EXAMPLE CLAUSES

A. A system comprising: one or more processors; and one or more non-transitory computer-readable media storing instructions executable by the one or more processors to: receive, via a graphical user interface (GUI), first instructions defining one or more rules associated with an outcome that corresponds to a particular healthcare application; receive second instructions defining a schema for translating the one or more rules into one or more logical expressions; convert the one or more rules into the one or more logical expressions based at least in part on the schema; access a plurality of data entries that are relevant to the particular healthcare application; apply the one or more logical expressions to the plurality of data entries; based at least in part on applying the one or more logical expressions to the plurality of data entries, identify a first data entry that satisfies the one or more rules; apply, at a substantially same time as the one or more logical expressions are applied to the plurality of data entries, a model to the plurality of data entries; based at least in part on applying the model to the plurality of data entries, identify a second data entry that is predicted to be associated with the outcome; generate an output identifying the first data entry and the second data entry; and determine an action associated with the particular healthcare application based at least in part on the output.

B. A system as paragraph A recites, wherein the action comprises at least one of generating a communication to send to one or more target members to offer a service provided by a healthcare management service provider; initiating an investigation into whether one or more healthcare related claims are fraudulent; mapping one or more healthcare related claims to a classification; validating one or more healthcare related claims based on a classification; routing one or more healthcare related claims based on a classification; or auditing healthcare data sources or healthcare reporting data.

C. A system as either paragraph A or B recites, wherein the instructions are executable by the one or more processors further to train the model based at least in part on a machine learning mechanism.

D. A system as any of paragraphs A-C recite, wherein: the GUI comprises a table having a plurality of column groups and a plurality of row groups; and the plurality of column groups and the plurality of row groups are associated with Boolean logic.

E. A system as paragraph D recites, wherein: individual column groups of the plurality of column groups are associated with conjunctive Boolean logic; and individual rows in a row group of the plurality of row groups are associated with disjunctive Boolean logic.

F. A system as any of paragraphs A-E recite, wherein the instructions are executable by the one or more processors further to: receive input from two or more expert-type users substantially simultaneously, the two or more expert-type users providing input from different devices; and update the GUI based at least in part on the input.

G. A computer-implemented method comprising: receiving, via a graphical user interface (GUI), first instructions defining one or more rules associated with an outcome that corresponds to a particular healthcare application; receiving second instructions defining a schema for translating the one or more rules into one or more logical expressions; converting the one or more rules into the one or more logical expressions based at least in part on the schema; accessing a plurality of data entries that are relevant to the particular healthcare application; applying the one or more logical expressions to the plurality of data entries; based at least in part on applying the one or more logical expressions to the plurality of data entries, identifying a first data entry that satisfies the one or more rules; applying a model to the plurality of data entries; based at least in part on applying the model to the plurality of data entries, identifying a second data entry that is predicted to be associated with the outcome; and generating an output identifying the first data entry and the second data entry.

H. A computer-implemented method as paragraph G recites, wherein: the one or more rules identify one or more attributes of a profile of one or more target members of a healthcare management service; the first data entry is associated with a first target member of the one or more target members; and the computer-implemented method further comprises identifying, based at least in part on the output, a recommendation for the first target member in view of at least one of healthcare program coverage available to the first target member, services offered by the healthcare management service, or healthcare needs of the first target member.

I. A computer-implemented method as either paragraph G or H recites, wherein: the one or more rules identify one or more attributes of a fraudulent claim; the first data entry is associated with a first claim; and the computer-implemented method further comprises providing an indication to initiate an investigation into whether the first claim is fraudulent based at least in part on the output.

J. A computer-implemented method as any of paragraphs G-I recite, wherein: the one or more rules identify one or more attributes for determining a classification of a claim; the first data entry is associated with a first claim; and the computer-implemented method further comprises providing an indication to initiate adjudication of the first claim based at least in part on the output.

K. A computer-implemented method as any of paragraphs G-J recite, wherein: the one or more rules identify one or more attributes for verifying a particular data entry; and the computer-implemented method further comprises verifying the first data entry based at least in part on the output.

L. One or more computer-readable media as any of paragraphs G-K recite, wherein determining the particular visual element comprises classifying the visual elements based at least in part on applying a binary classifier to at least one of the lexical features and gaze features.

M. A device comprising one or more processors and one or more computer readable media as any of paragraphs G-K recite.

N. A computer-implemented method comprising: means for receiving, via a graphical user interface (GUI), first instructions defining one or more rules associated with an outcome that corresponds to a particular healthcare application; receiving second instructions defining a schema for translating the one or more rules into one or more logical expressions; means for converting the one or more rules into the one or more logical expressions based at least in part on the schema; means for accessing a plurality of data entries that are relevant to the particular healthcare application; applying the one or more logical expressions to the plurality of data entries; means for, based at least in part on applying the one or more logical expressions to the plurality of data entries, identifying a first data entry that satisfies the one or more rules; applying a model to the plurality of data entries; means for, based at least in part on applying the model to the plurality of data entries, identifying a second data entry that is predicted to be associated with the outcome; and means for generating an output identifying the first data entry and the second data entry.

O. A computer-implemented method as paragraph N recites, wherein: the one or more rules identify one or more attributes of a profile of one or more target members of a healthcare management service; the first data entry is associated with a first target member of the one or more target members; and the computer-implemented method further comprises means for identifying, based at least in part on the output, a recommendation for the first target member in view of at least one of healthcare program coverage available to the first target member, services offered by the healthcare management service, or healthcare needs of the first target member.

P. A computer-implemented method as either paragraph N or O recites, wherein: the one or more rules identify one or more attributes of a fraudulent claim; the first data entry is associated with a first claim; and the computer-implemented method further comprises means for providing an indication to initiate an investigation into whether the first claim is fraudulent based at least in part on the output.

Q. A computer-implemented method as any of paragraphs N-P recite, wherein: the one or more rules identify one or more attributes for determining a classification of a claim; the first data entry is associated with a first claim; and the computer-implemented method further comprises means for providing an indication to initiate adjudication of the first claim based at least in part on the output.

R. A computer-implemented method as any of paragraphs N-Q recite, wherein: the one or more rules identify one or more attributes for verifying a particular data entry; and the computer-implemented method further comprises means for verifying the first data entry based at least in part on the output.

S. A system comprising: one or more processors; and one or more non-transitory computer-readable media storing instructions executable by the one or more processors to: access data associated with one or more individuals, the data associated with at least one of healthcare related claims, healthcare program authorizations, healthcare program utilization, engagement, or preferences; access service data associated with one or more services offered by a healthcare management service; determine, based at least in part on the data and the service data, one or more attributes associated with a profile associated with a class of target members for targeting one or more services offered by the healthcare management service; receive, via a graphical user interface (GUI), first instructions defining one or more user-editable rules for identifying the one or more target members of the class of target members associated with the profile; receive second instructions defining a schema for translating the one or more user-editable rules into one or more computer-executable logical expressions; convert the one or more user-editable rules into the one or more computer-executable logical expressions based at least in part on the schema; apply the one or more computer-executable logical expressions to the data; based at least in part on applying the one or more computer-executable logical expressions to the data, identify a first target member associated with the profile; apply, in parallel with applying the one or more computer-executable logical expressions to the data, a model to the data, the model having been trained by a machine learning mechanism; based at least in part on applying the model to the data, identify a second target member predicted to be associated with the profile; determine that the first target member and the second target member are associated with the profile; and send, to at least one of a first device operated by the first target member or a second device operated by the second target member, a communication to at least one of the first target member or the second target member to provide access to a service of the one or more services offered by the healthcare management service provider.

T. A system as paragraph S recites, wherein: the GUI comprises a table having a plurality of column groups and a plurality of row groups; a first row group of the plurality of row groups corresponds to a rule of the one or more rules, the rule corresponding to an attribute of the one or more attributes; and a first column group of the plurality of column groups corresponds to a partial condition for satisfying the rule.

U. A system as paragraph T recites, wherein: the first column group includes one or more columns, each column of the one or more columns corresponding to a parameter; and the first row group includes at least one row corresponding to one or more parameters associated with an option for determining that the partial condition is true.

V. A system as paragraph T recites, wherein: the first column group includes one or more columns, each column of the one or more columns corresponding to a parameter; the first row group includes two or more rows; a first row of the two or more rows corresponding to one or more first parameters associated with a first option for determining that the partial condition is true; and a second row of the two or more rows corresponding to one or more second parameters associated with a second option for determining that the partial condition is true, wherein satisfaction of the partial condition via the first option or the second option is sufficient to determine that particular data associated with the first target member satisfies the partial condition.

W. A system as paragraph T recites, wherein identifying at least the first target member associated with the profile comprises: determining, based at least in part on applying the one or more computer-executable logical expressions to the data, that particular data associated with the first target member satisfies each partial condition of the rule; and identifying that the first target member is associated with the profile based at least in part on determining that the particular data satisfies each partial condition of the rule.

X. A system as any of paragraphs S-W recite, wherein the instructions are executable by the one or more processors further to: receive the first instructions defining the one or more user-editable rules from one or more third devices operated by one or more expert-type users; receive the second instructions defining the schema from a fourth device operated by a power user; and receive a third set of instructions defining how to apply the one or more computer-executable logical expressions and the model from a fifth device operated by a programmer.

Y. A system as any of paragraphs S-X recite, wherein the first target member and the second target member are different target members and the instructions are executable by the one or more processors further to: determine a healthcare characteristic shared by the first target member and the second target member; and generate the communication to instruct at least the first target member or the second target member to address the healthcare characteristic.

Z. A system as any of paragraphs S-Y recite, wherein the instructions are executable by the one or more processors further to: determine at least one previously unengaged product partner, healthcare program benefit, or healthcare program incentive to recommend to at least the first target member; generate a recommendation for recommending the at least one previously unengaged product partner, healthcare program benefit, or healthcare program incentive to at least the first target member; and send the recommendation, via the communication, to at least the first device.

AA. A system any of paragraphs S-Z recite, wherein the instructions are executable by the one or more processors further to: determine at least one healthcare program change to recommend to an employer of the first target member; generate a recommendation for the at least one healthcare plan change to the employer; and send the recommendation to a third device operated by the employer.

What is claimed is:

1. A computer-implemented method, performed on a computing system, comprising:
    receiving first instructions, provided by a first user via a graphical user interface,
    defining one or more user-designated rules identifying one or more attributes of at least one of:
        a claim associated with a healthcare management service provider, or
        a target member of the healthcare management service provider;
    receiving second instructions, provided by a second user, defining a schema for translating the one or more user-designated rules into one or more logical expressions, wherein:
        the first user and the second user are distinct from one another, and
        the second user is a power-type user associated with access-control settings that grant the second user access to different features of the computing system than the first user;
    converting the one or more user-designated rules into the one or more logical expressions based at least in part on the schema;
    accessing a plurality of data entries associated with the healthcare management service provider;
    identifying a first data entry that satisfies the one or more user-designated rules, based at least in part on applying the one or more logical expressions to the plurality of data entries;
    identifying a second data entry, in parallel to identifying the first data entry, based at least in part on applying a model to the plurality of data entries;
    determining a comparison between:
        the first data entry that satisfies the one or more user-designated rules, and
        the second data entry identified by applying the model;
    generating an output based at least in part on the first data entry, the second data entry, and the comparison, wherein the output indicates at least one of the first data entry or the second data entry; and
    performing an operation associated with the at least one of the first data entry or the second data entry indicated by the output.

2. The computer-implemented method of claim 1, wherein:
    at least one of the first data entry or the second data entry is associated with the claim, and
    the operation comprises providing an indication to initiate adjudication of the claim.

3. The computer-implemented method of claim 1, wherein:

at least one of the first data entry or the second data entry is associated with the claim, and the operation comprises providing an indication to initiate an investigation into whether the claim is fraudulent.

4. The computer-implemented method of claim 1, wherein:

at least one of the first data entry or the second data entry is associated with the claim, and the operation comprises verifying the claim.

5. The computer-implemented method of claim 1, wherein:

at least one of the first data entry or the second data entry is associated with the target member, and the operation comprises identifying a recommendation, for the target member, associated with at least one of:

available healthcare program coverage, services offered by the healthcare management service provider, or healthcare needs of the target member.

6. The computer-implemented method of claim 1, wherein:

at least one of the first data entry or the second data entry is associated with the target member, and the operation comprises generating at least one healthcare program change to recommend to an employer of the target member.

7. The computer-implemented method of claim 1, further comprising:

receiving the first instructions defining the one or more user-designated rules from a first device operated by the first user;

receiving the second instructions defining the schema from a second device operated by the second user; and receiving third instructions defining how to apply the one or more logical expressions and the model from a third device operated by a programmer.

8. The computer-implemented method of claim 1, wherein:

the one or more user-designated rules are user-editable by the first user by inputting the first instructions via the graphical user interface, the one or more user-designated rules are not computer-executable, and the one or more logical expressions, generated by converting the one or more user-designated rules based at least on in part on the schema, are computer-executable.

9. The computer-implemented method of claim 1, wherein:

the comparison determines that the first data entry and the second data entry are duplicative or in conflict, and the computer-implemented method further comprises generating the output by performing a deduplication process or a conflict resolution process to remove one of the first data entry and the second data entry from being indicated by the output.

10. A computing system comprising:

one or more processors; and one or more non-transitory computer-readable media storing instructions that, when executed by the one or more processors, cause the computing system to perform operations comprising:

receiving first instructions, provided by a first user via a graphical user interface, defining one or more user-designated rules identifying one or more attributes of at least one of:

a claim associated with a healthcare management service provider, or a target member of the healthcare management service provider;

receiving second instructions, provided by a second user, defining a schema for translating the one or more user-designated rules into one or more logical expressions, wherein:

the first user and the second user are distinct from one another, and the second user is a power-type user associated with access-control settings that grant the second user access to different features of the computing system than the first user;

converting the one or more user-designated rules into the one or more logical expressions based at least in part on the schema;

accessing a plurality of data entries associated with the healthcare management service provider;

identifying a first data entry that satisfies the one or more user-designated rules, based at least in part on applying the one or more logical expressions to the plurality of data entries;

identifying a second data entry, in parallel to identifying the first data entry, based at least in part on applying a model to the plurality of data entries;

determining a comparison between:

the first data entry that satisfies the one or more user-designated rules, and the second data entry identified by applying the model;

generating an output based at least in part on the first data entry, the second data entry, and the comparison, wherein the output indicates at least one of the first data entry or the second data entry; and performing an operation associated with the at least one of the first data entry or the second data entry indicated by the output.

11. The computing system of claim 10, wherein:

at least one of the first data entry or the second data entry is associated with the claim, and the operation comprises providing an indication to initiate adjudication of the claim.

12. The computing system of claim 10, wherein:

at least one of the first data entry or the second data entry is associated with the claim, and the operation comprises providing an indication to initiate an investigation into whether the claim is fraudulent.

13. The computing system of claim 10, wherein:

at least one of the first data entry or the second data entry is associated with the claim, and the operation comprises verifying the claim.

14. The computing system of claim 10, wherein:

at least one of the first data entry or the second data entry is associated with the target member, and the operation comprises identifying a recommendation, for the target member, associated with at least one of:

available healthcare program coverage, services offered by the healthcare management service provider, or healthcare needs of the target member.

15. The computing system of claim 10, wherein:

at least one of the first data entry or the second data entry is associated with the target member, and the operation comprises generating at least one healthcare program change to recommend to an employer of the target member.

16. The computing system of claim 10, the operations further comprising:
   receiving the first instructions defining the one or more user-designated rules from a first device operated by the first user;
   receiving the second instructions defining the schema from a second device operated by the second user; and
   receiving third instructions defining how to apply the one or more logical expressions and the model from a third device operated by a programmer.

17. The computing system of claim 10, wherein:
   the one or more user-designated rules are user-editable by the first user by inputting the first instructions via the graphical user interface,
   the one or more user-designated rules are not computer-executable, and
   the one or more logical expressions, generated by converting the one or more user-designated rules based at least on in part on the schema, are computer-executable.

18. The computing system of claim 10, wherein:
   the comparison determines that the first data entry and the second data entry are duplicative or in conflict, and
   the operations further comprise generating the output by performing a deduplication process or a conflict resolution process to remove one of the first data entry and the second data entry from being indicated by the output.

19. The computer-implemented method of claim 1, wherein:
   the comparison determines that the first data entry and the second data entry are not duplicative and are not in conflict, and
   the output indicates both the first data entry and the second data entry.

20. The computing system of claim 10, wherein:
   the comparison determines that the first data entry and the second data entry are not duplicative and are not in conflict, and
   the output indicates both the first data entry and the second data entry.

* * * * *